(12) United States Patent
Ranft

(10) Patent No.: US 8,882,778 B2
(45) Date of Patent: Nov. 11, 2014

(54) INSTRUMENTS FOR CARRYING OUT AN OPERATING PROCEDURE ON A JOINT

(75) Inventor: Christoph Ranft, Kiel (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 681 days.

(21) Appl. No.: 12/742,191

(22) PCT Filed: Nov. 10, 2008

(86) PCT No.: PCT/EP2008/009479
§ 371 (c)(1),
(2), (4) Date: May 10, 2010

(87) PCT Pub. No.: WO2009/059800
PCT Pub. Date: May 14, 2009

(65) Prior Publication Data
US 2010/0274251 A1    Oct. 28, 2010

(30) Foreign Application Priority Data

Nov. 10, 2007 (DE) .................. 10 2007 053 702
Aug. 22, 2008 (DE) .................. 10 2008 039 241

(51) Int. Cl.
| A61B 17/56 | (2006.01) |
| A61B 17/15 | (2006.01) |
| A61B 17/02 | (2006.01) |
| A61F 2/42  | (2006.01) |
| A61B 17/16 | (2006.01) |
| A61F 2/46  | (2006.01) |
| A61B 17/17 | (2006.01) |
| A61F 2/30  | (2006.01) |
| A61B 17/14 | (2006.01) |

(52) U.S. Cl.
CPC ............. *A61B 17/15* (2013.01); *A61B 17/1703* (2013.01); *A61B 2017/1782* (2013.01); *A61B 17/1725* (2013.01); *A61F 2002/30624* (2013.01); *A61B 17/02* (2013.01); *A61F 2/4241* (2013.01); *A61B 17/1686* (2013.01); *A61F 2002/4243* (2013.01); *A61B 17/14* (2013.01); *A61B 2017/1602* (2013.01); *A61F 2/4606* (2013.01)
USPC .......................................................... 606/87

(58) Field of Classification Search
USPC ....... 606/53, 54, 57, 58, 80, 82, 86 R, 87, 96, 606/130; 600/233; 623/21.11, 21.15–21.19
See application file for complete search history.

(56) References Cited

U.S. PATENT DOCUMENTS 4,620,539 A * 11/1986 Andrews et al. .............. 606/180
5,409,493 A *  4/1995 Greenberg ...................... 606/96

(Continued)

FOREIGN PATENT DOCUMENTS

| FR | 2 669 215 A1   | 5/1992 |
| WO | 97/05836 A1    | 2/1997 |
| WO | 2005/027759 A1 | 3/2005 |

OTHER PUBLICATIONS

International Preliminary Report on Patentability, issued on May 11, 2010, in International Application No. PCT/EP2008/009479.

*Primary Examiner* — Christian Sevilla
(74) *Attorney, Agent, or Firm* — Panitch Schwarze Belisario & Nadel LLP

(57) ABSTRACT

The invention concerns instruments for carrying out an operating procedure on a finger joint, in which the damaged joint 4 is radially milled out by means of the instruments and is replaced by a hinge prosthesis 50.

24 Claims, 24 Drawing Sheets

(56) References Cited

U.S. PATENT DOCUMENTS

| | | | |
|---|---|---|---|
| 5,582,577 A * | 12/1996 | Lund et al. | 600/204 |
| 6,030,391 A | 2/2000 | Brainard et al. | |
| 6,129,729 A * | 10/2000 | Snyder | 606/916 |
| 6,152,871 A * | 11/2000 | Foley et al. | 600/114 |
| 2005/0149026 A1 * | 7/2005 | Butler et al. | 606/69 |
| 2005/0216026 A1 | 9/2005 | Culbert | |
| 2005/0245935 A1 * | 11/2005 | Casey et al. | 606/82 |

* cited by examiner

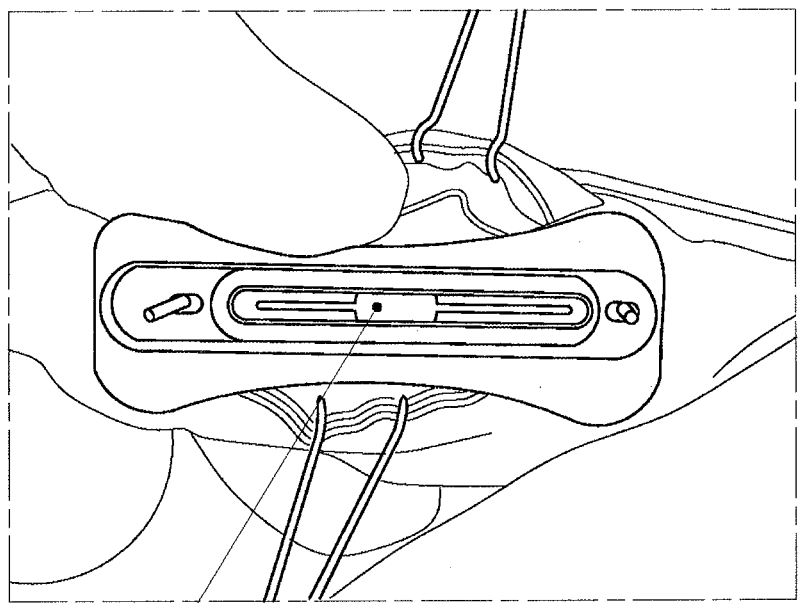
40    Fig. 19
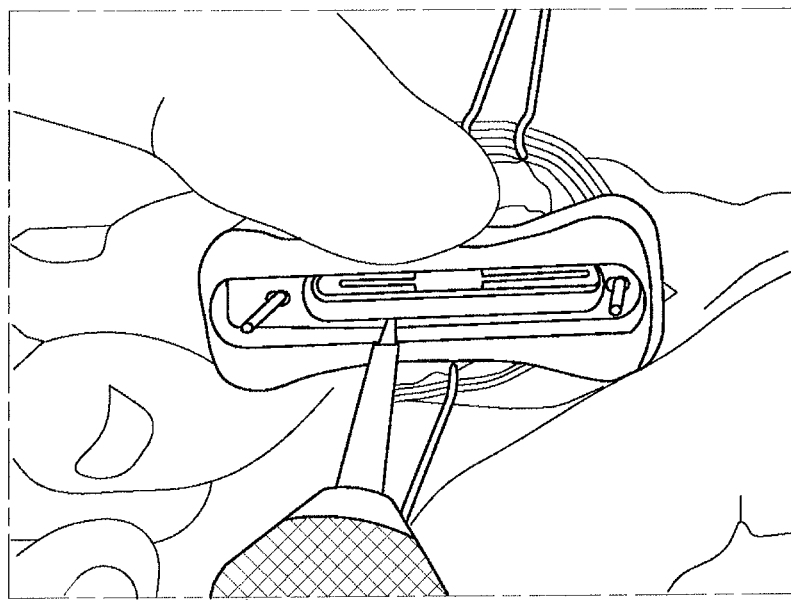
20    Fig. 20

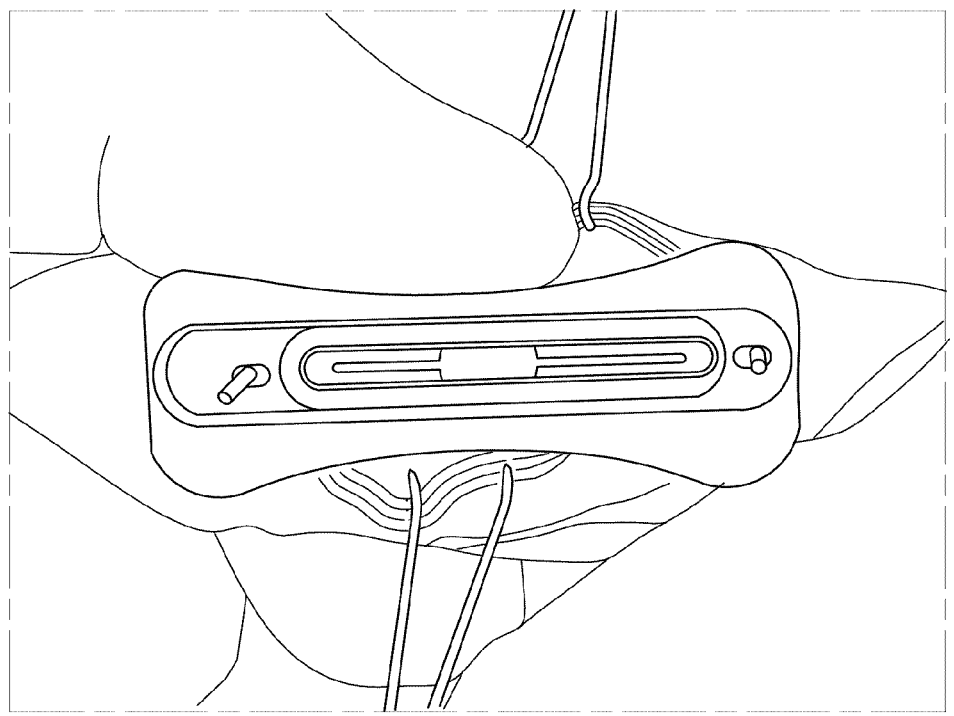
Fig. 23
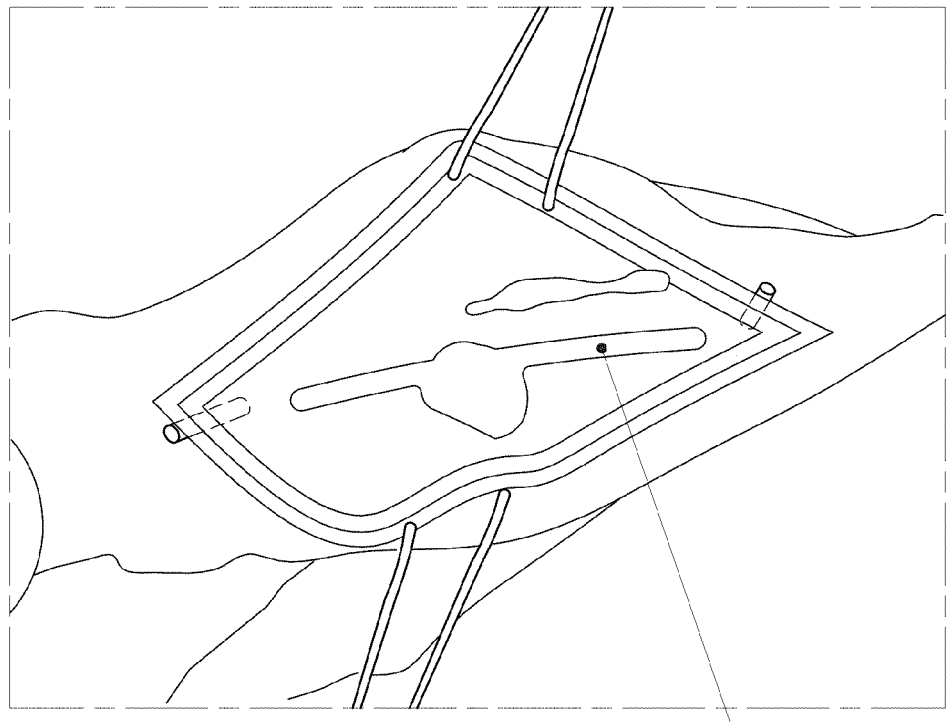
Fig. 24    44

INSTRUMENTS FOR CARRYING OUT AN OPERATING PROCEDURE ON A JOINT

CROSS-REFERENCE TO RELATED APPLICATIONS

This application is a Section 371 of International Application No. PCT/EP2008/009479, filed Nov. 10, 2008, which was published in the English language on May 14, 2009, under International Publication No. WO 2009/059800 A3 and the disclosure of which is incorporated herein by reference.

BACKGROUND OF THE INVENTION

The invention concerns instruments for carrying out an operating procedure on the joint of a patient, in particular a finger joint. In addition the invention concerns an operating method of replacing a joint of a patient, in particular a finger joint, preferably a finger middle joint.

In any gripping function by the hand the middle joint (the PIP joint) of the finger implements almost the greatest and most important part of the bending power of the finger and is therefore indispensable in its ability to operate for the essential forms of gripping action by the hand (gripping items forcibly, gripping large items, gripping keys gripping combs, gripping writing implements and so forth). If the function of the PIP joint is reduced due to pain and/or a restriction on movement ultimately the overall function of the hand also suffers. Pain cannot be permanently treated with medication as medications loose their effectiveness and often cause undesired incompatibilities and have side-effects.

External immobilisation is extremely impracticable and uncomfortable in everyday life, and in addition the function of the finger is markedly impeded. That ultimately applies also to 'internal' immobilisation of the injured joint, which immobilisation was and still is implemented in the form of a functionally appropriate or individually desired position by means of what is referred to as arthrodesis of the PIP joint, that is to say bone fusion of the middle and base joint. Freedom from pain can in that way actually always be achieved, but the stiffening of the joint is actually not acceptable having regard to the above-outlined enormous importance of the PIP joint in terms of the overall functioning of the hand. In that respect it is in principle to be considered that increasingly also and in particular older people are reliant on proper operability of their hands as many cannot manage for themselves and their own wish for independence and the necessity for independence are continually on the rise.

Many different endeavours have been made over many years to arrive at suitable solutions for joint replacement on the fingers. Hitherto however it has not yet been possible for any design to prove crucially successful as none adequately complies with all important target criteria.

Implants used at the present time suffer from certain disadvantages and do not meet the target criteria.

On the one hand Swanson Silastic spacers are used, which in spite of the induction of foreign body granuloma, the risk of material fracture and guidance instability, often give astonishing results, in particular in relation to rheumatoid arthritis. Those movable spacers which actually do not represent a joint have therefore certainly a firm place in relation to this indication. The limit of what is viable however is rapidly reached therewith, with a high level of substance loss and advanced destruction.

Present coupled 'genuine' joint implants such as for example the St. George endoprosthesis are inserted dorsally and cemented in place, but frequently exhibit loosening effects and often involve a poor function, which is to be attributed to the high tensile and frictional forces, for which reason that method is inadequate.

Nowadays the idea of surface replacement with reconstruction of the utmost accuracy of the predetermined anatomy is favoured, and non-coupled implants in the form of the pyrocarbon endoprosthesis and the moje ceramic implant are the leading representatives. As anatomically the middle joint is also not a pure hinge joint but involves a rotational-sliding movement, the endeavour is ultimately the most natural motion without potentially harmful tensile and rotational forces. The previous operational observations and investigations however could not demonstrate that as a rule the endoprostheses involve bony integration, on the contrary they rather do not grow into place, and exhibit migration and bone extension phenomena which prevent a good functional result.

In addition those endoprostheses have to be fitted by a stretching apparatus, which precisely signifies injury to that enormously sensitive functional structure, with the consequences of limited early functionality, fibroses and deformations which possibly necessitate further interventions for releasing the joint, as well as shrinkage phenomena which sometimes result in stretching contraction. The attempt to implant the endoprosthesis by way of the flexural side is intended to represent an alternative, but here crucially sensitive tissue is also injured, which can limit the function due to healing effects.

The partially necessary removal of such joints then also impressively shows that, due to the respective prosthesis shank, bone substance has scarcely remained besides the cortical 'sheath' of the phalanges, a hollow tube which requires a great deal of sound bone substance for an arthrodesis which is then necessary.

The indications in respect of such implants arise out of the described facts: lack of early mobilisation mean that contracted, pre-operated joints with tendon deformation and adhesions appear inappropriate, and equally joint instabilities are not a suitable condition.

Long years of surgical activity on hands mean that the critical operator is always discontent with the fact that the motor functional structures on the fingers, the extension and flexing tendons in their complexity and the sensitivity linked thereto, in spite of the most careful treatment, always leave behind healing symptoms with the environment, which often crucially limit the finger function. Secondary tendon dissolutions are linked to extreme risks and can often leave behind results which are equally poor as previously. If exercise is taken too early after a tendon suture the tissue possibly does not stick together but then there is a functional limitation due to suture insufficiency. It would be best for those structures not to be surgically treated at all if that does not have to be done.

In addition in the case of a disturbance to a finger function finger reconstruction by joint replacement should not be ruined by sound tissue being damaged in the course of the operation.

BRIEF SUMMARY OF THE INVENTION

The object of the present invention is therefore that of providing instruments for the insertion of a finger joint prosthesis, and a treatment method which is capable of performing the flexing and elongation function of the joint, in particular the PIP joint, at best in the sound anatomically predetermined extent of movement and direction of movement so that the harmonic juxtaposition and co-operation of the fingers in regard to the gripping functions are not disturbed. The alloplastic joint must be anchored in the bone in such a way that it does not depart from its intended position and thus would again endanger the function involved. It should not further destroy the remaining bone (the phalanges do not afford here an excessively great resource) due to use of the joint and it should be stable in its functional form so that the finger can be subjected to load.

That object is attained by an instrument for carrying out an operating procedure on the joint of a patient, in particular on a finger joint, which includes at least the following components:

- a fixing frame for fixing a finger in a straight position in the course of an operation for milling out a joint cylinder of the finger with a rigid structure for forming a receiving space for the finger and a drilling slide which is displaceable on the structure and which is fixable in any reference positions and which has a positioning bar with a guide opening for relatively movably receiving a joint milling cutter or a centering sleeve and a plurality of positioning holes,
- a drilling slide with a positioning bar which extends in a longitudinal direction and which has a guide opening extending transversely through same and laterally of said guide opening positioning holes, and which is provided with means for guiding engagement into the fixing frame, as well as a spacer element which extends transversely with respect to the positioning bar and with which the positioning bar is fixable in various reference positions which can be selected as desired in relation to the fixing frame,
- a centering sleeve comprising a cylindrical main body adapted for insertion into the guide opening of the drilling slide which at one end has a peripherally extending shoulder and centrally has a receiving opening for an aiming wire, and
- a rotary axis aiming device for exactly milling out the joint cylinder.

That instrument set makes it possible to achieve particularly accurate positioning and fixing of the joint for precisely carrying out the operating procedure. The rigid fixing frame serves in that case as a fixing means for precisely positioning the joint in the extended position.

The material of the endoprosthesis used is preferably biocompatible and 'low-wear' so that the tissue is not subjected to secondary damage in another way. The endoprosthesis must technically be fitted in such a way that as far as possible sound 'tissue resource' of any kind is also always treated carefully. That must apply in particular to the extremely sensitive functional structures of the flexing and extension tendons. The joint should be capable of being moved as early as possible after the implantation operation so as to avoid sticking and healing adhesions in respect of the specified functional structures. Finally the endoprosthesis should have long durability in the bone, it should cover an indication spectrum which is as comprehensive as possible and it should have a secure reliable technical implantation route.

The invention is based on the essential concept of laterally implanting the endoprosthesis: lateral access to the finger circumvents the 'at-risk' extending and flexing side of the finger and leaves the above-mentioned functional tissue substantially unaffected. It is only necessary to remove a lateral ligament of the finger joint, then the joint is there. All operative necessities can be implemented by way of that access, such as for example removing osteophytes, and even tendon dissolution in relation to joints which have stiffened as a result of post-operative trauma.

To maintain as much bony substance of the phalanges as possible, in accordance with the invention only the joint is removed and an anchoring option is provided for the endoprosthesis, which is so stable that early post-operative exercise of the joint becomes a possibility.

The joint fitted in accordance with the invention is stable and preferably made from a material which is inert and easily incorporated by the bone.

Even if anatomically no hinge is involved, nonetheless it was possible from innumerable experience with care results after middle joint fractures to speculate that nature tolerates 'minor errors'. As at least in a few cases after implantation of a St. George hinge endoprosthesis it was possible to identify very good results (in spite of all the above-mentioned problems!), the mechanism of the hinge alone could not be the limiting factor.

Thus in accordance with the invention in the context of the 'constructive avoidance strategy' a coupled titanium hinge endoprosthesis, coated with hydroxyapatite and having a polyethylene contact surface was developed, which is implanted from the mediolateral side of a finger and which is primarily stably screwed in the bone.

Thus in accordance with the invention, according to the previous clinical experience, the target criteria are achieved at least in the short term:

- avoiding injury to the tendons,
- as little bony substance loss as possible,
- stable guidance for the implant,
- preferably biocompatibility of the implant,
- technically secure placement,
- high level of bony integration capability in spite of early mobility of the joint,
- very good mobility and load-carrying capability on the part of the implant, and
- a broad indication spectrum.

Clinical study hitherto shows that a quite wide indication spectrum applies, in a placement of this endoprosthesis.

Firstly the ideal indication is the painful 'normal' joint arthrosis with motion deficit and loading pain. Even large osteophyte structures do not represent a major obstacle. 'Inflammatory' arthroses do not form an exception with good bone substance as synovialectomies are possible by way of the mediolateral access without any problems.

In addition it is possible to treat post-traumatic arthroses even with axis errors. As the endoprosthesis is mediolaterally implanted from both sides, axis corrections are possible in that way. Hinge damage with contraction and tendon healing adhesions represent a further indication as even extensive tendon dissolutions are possible by way of the access, while maintaining the structure, and the early mobilisability then also makes indispensable exercise treatment for promoting and maintaining the joint function possible.

Post-infection damage to the joint represents a relative indication. In some cases the overall complex of bone substance, functional apparatus and soft partial sheathing has to be assessed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Further details, advantages and features of the invention will be apparent from the part of the description hereinafter, in which an embodiment by way of example of the device according to the invention is described in greater detail by reference to three drawings in which:

FIGS. 1 to 39 show the operating procedure according to the invention;

DETAILED DESCRIPTION OF THE INVENTION

Figure 1:
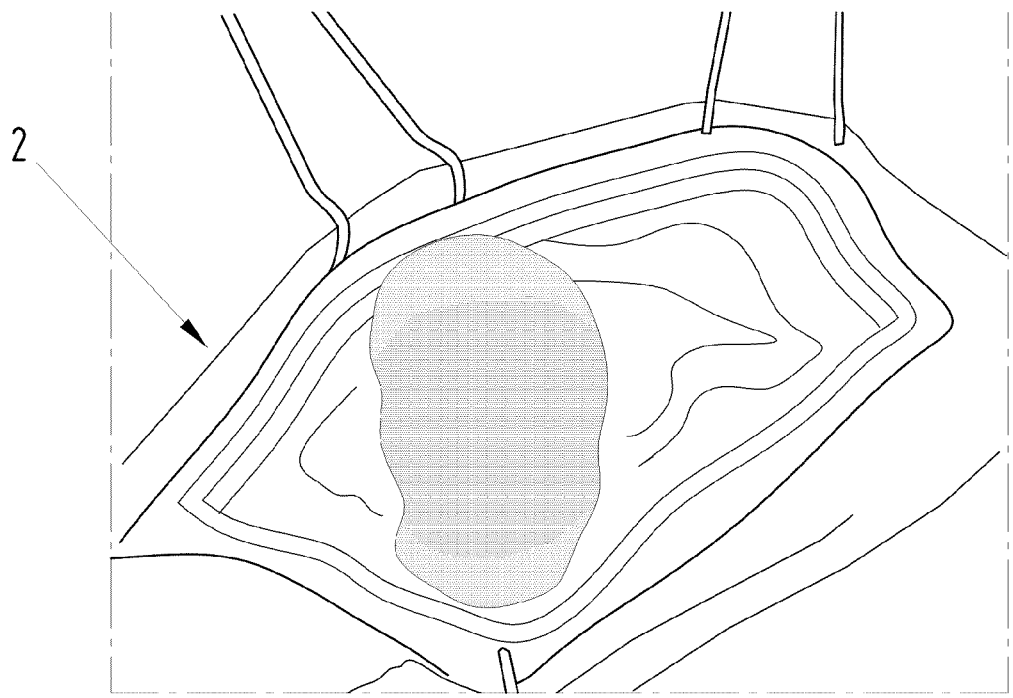
Figure 2:
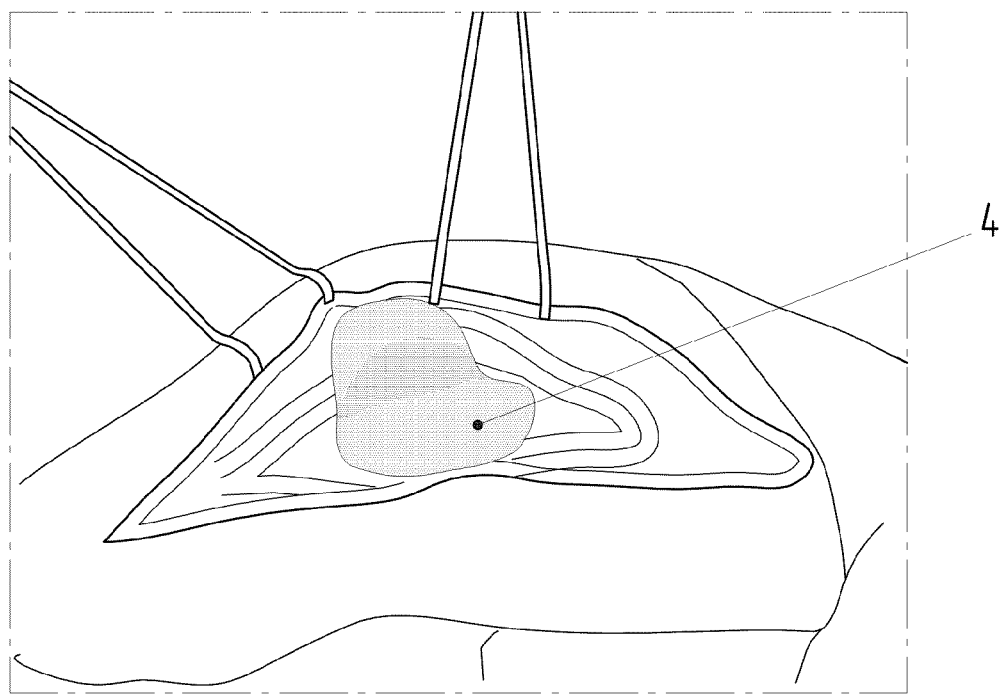

In accordance with the view in FIG. 1 access is effected mediolaterally and radially at a middle finger 2 at the right over a length of about 4-5 cm. The skin soft partial sheath is prepared, with the vessel and nerve structures being carefully treated. That is then followed, as shown in FIG. 2, by presentation of the Landsmeer ligament, severing thereof, and dorsal displacement of the extension apparatus after the opening of the joint 4.

Figure 3:
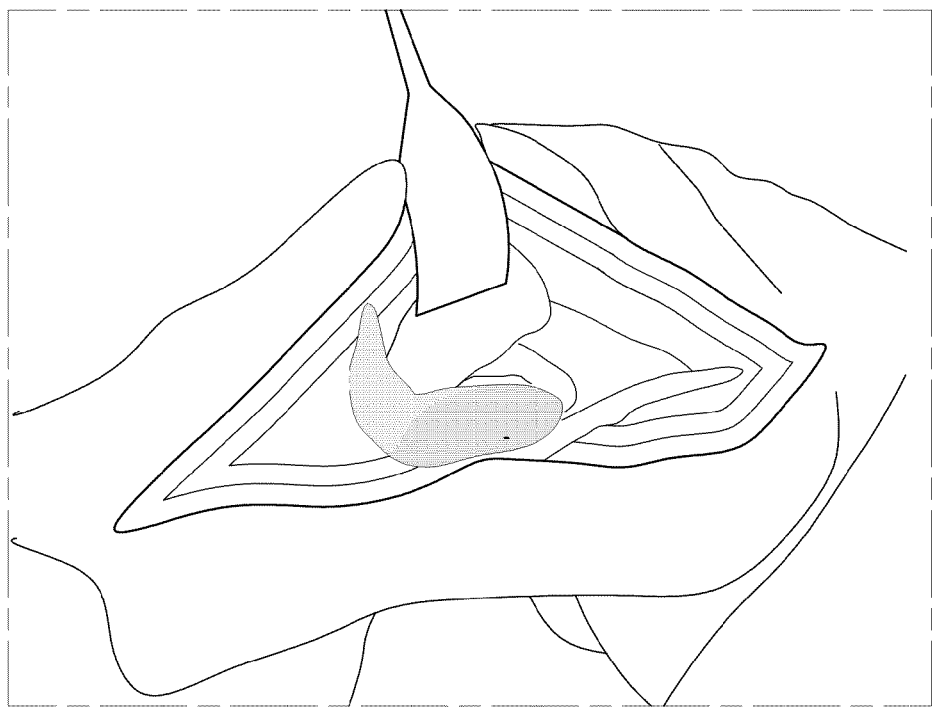
Figure 4:
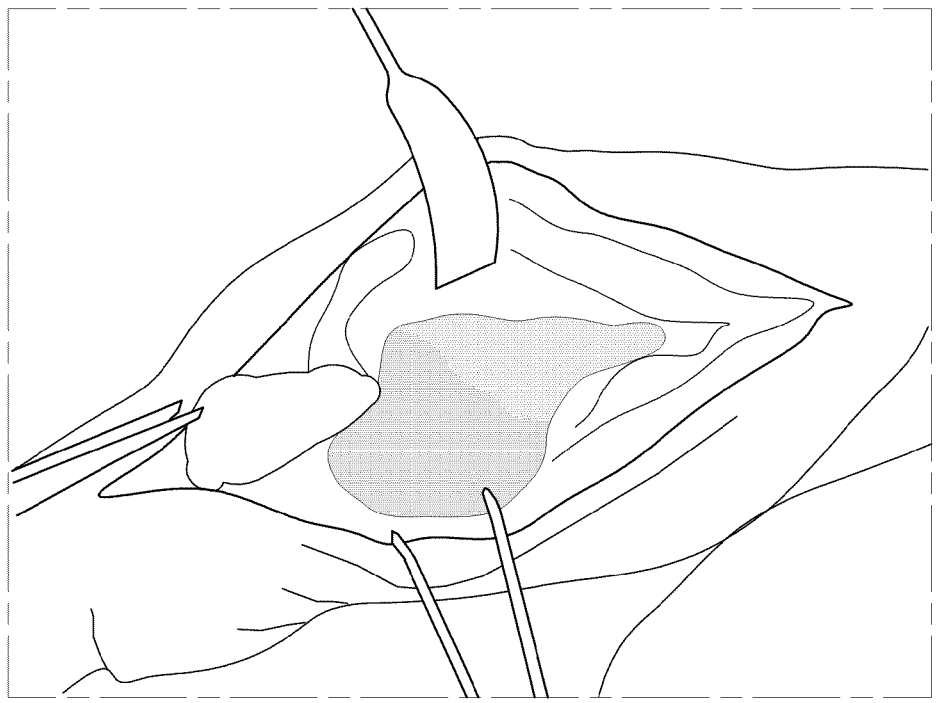
Figure 5:
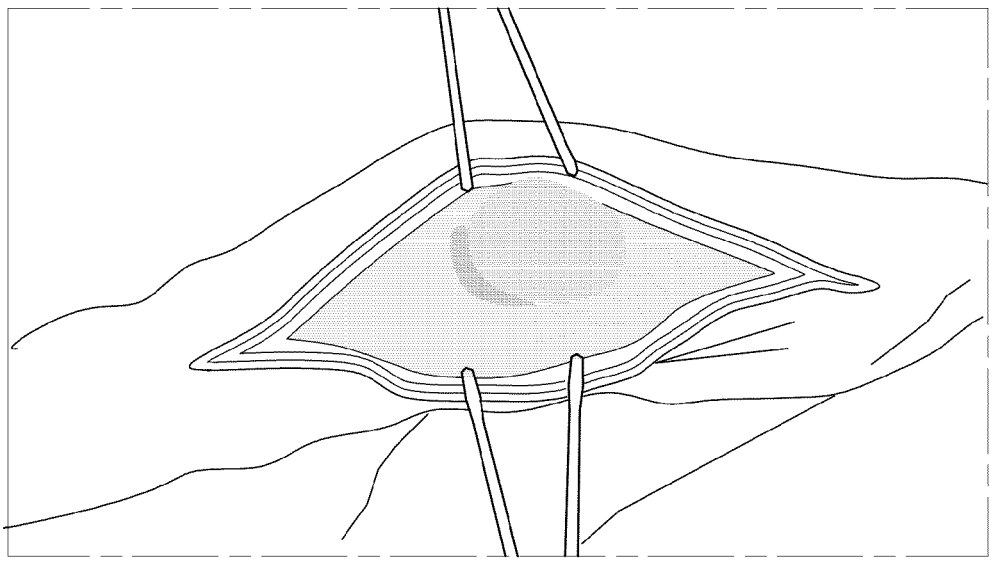

Then, as shown in FIG. 3, that is followed by the removal of joint osteophytes with the hollow gouge forceps and as shown in FIG. 4 resection of the radial collateral ligament.

Figure 6:
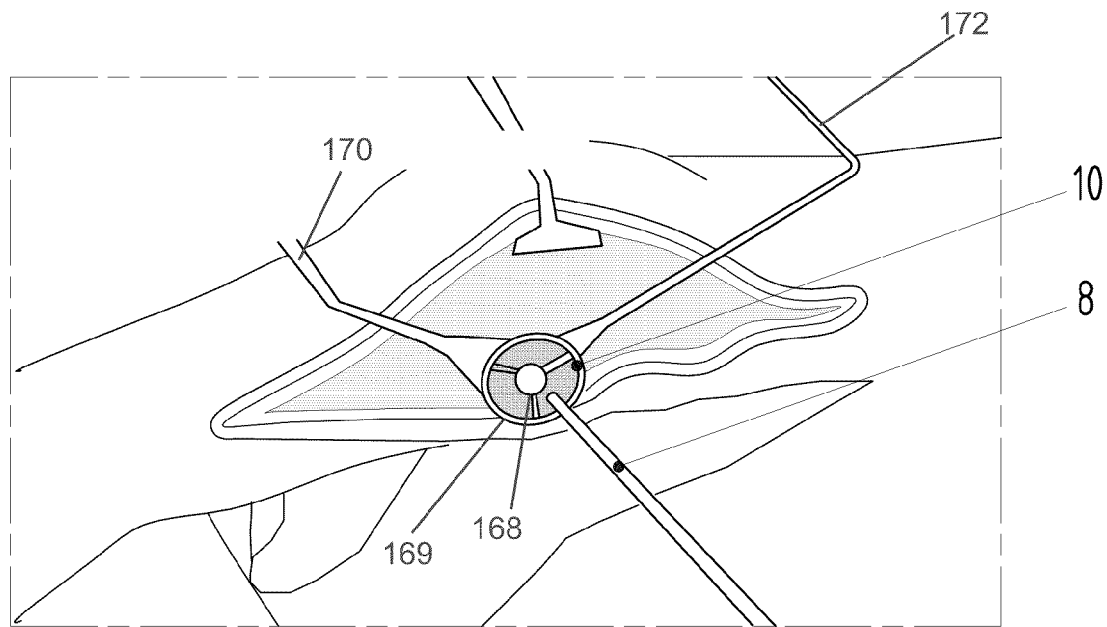
Figure 52:
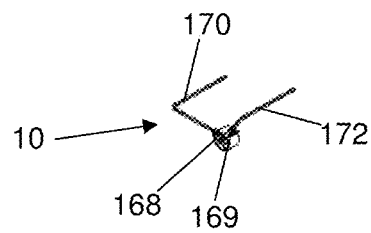
FIG. 52 shows a perspective view of the rotary axis aiming device.

After resection of the collateral ligament 6 a rotary axis aiming wire 8 which is preferably of a diameter of 1.2 mm, for the rotary axis of the joint 4, is placed on the lateral base phalanx head in such a way that the axis of the joint 4 is in palmar-proximal relationship. That adopts a central position in respect of the rotary axis which in principle actually moves. In FIG. 6 the rotary axis aiming device 10 which is shown in greater detail in FIG. 52 is set in place for checking the size and position of the joint cylinders to be resectioned.

Figure 7:
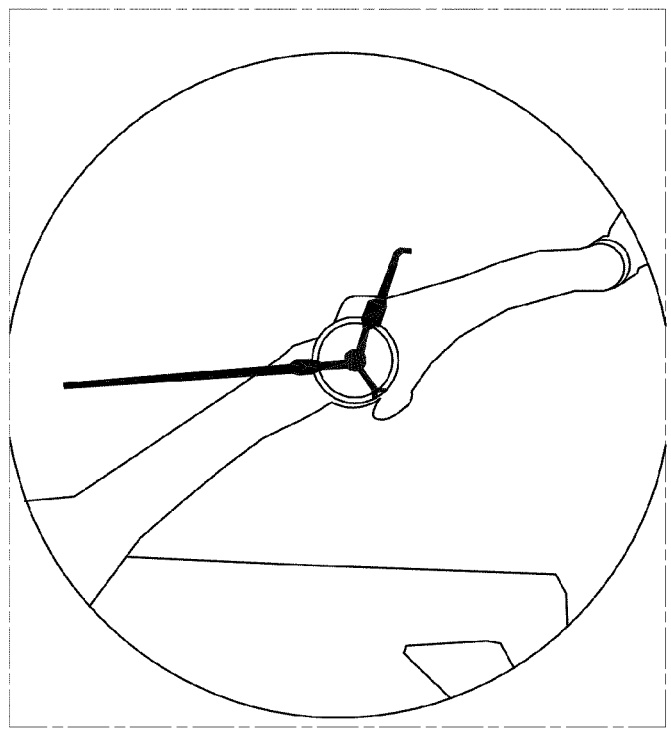
Figure 8:
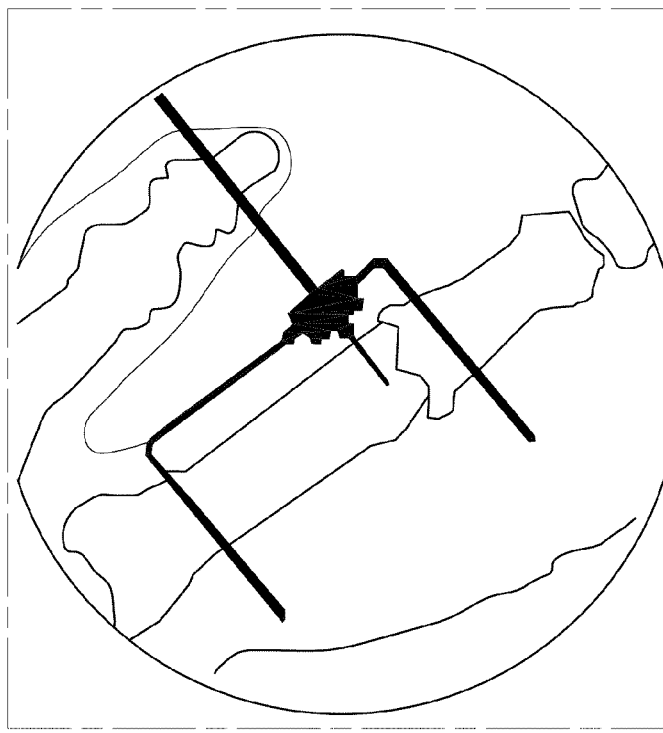

As shown in FIGS. 7 and 8, the correct position of the rotary axis is checked in both planes by the use of an image converter. In that respect the size and position of the joint cylinder to be resectioned is also again checked.

Figure 9:
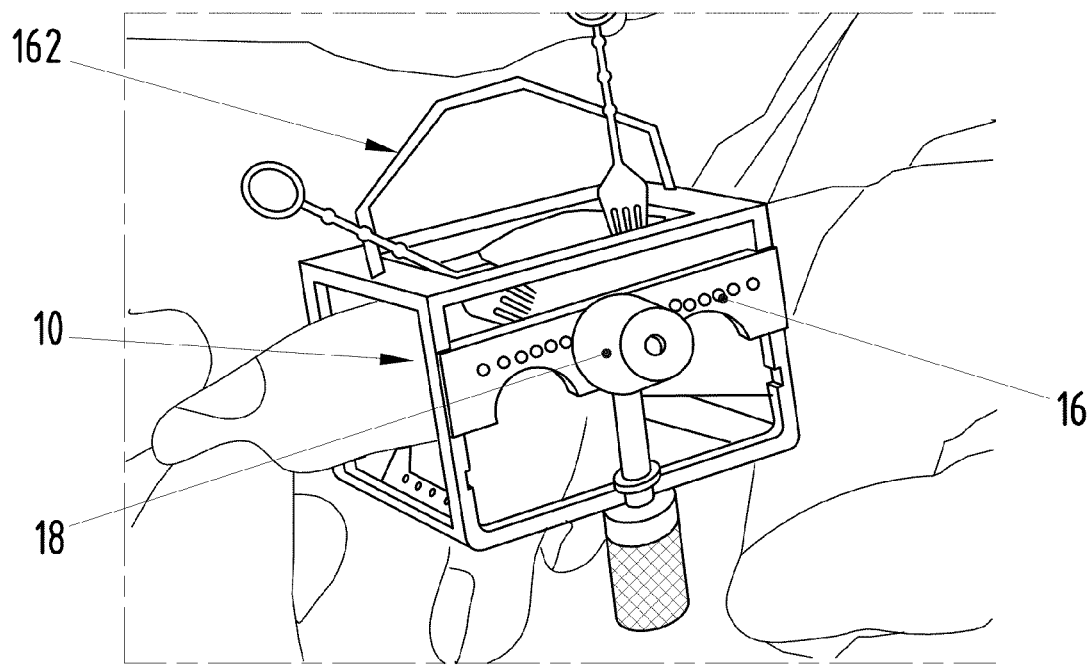
Figure 10:
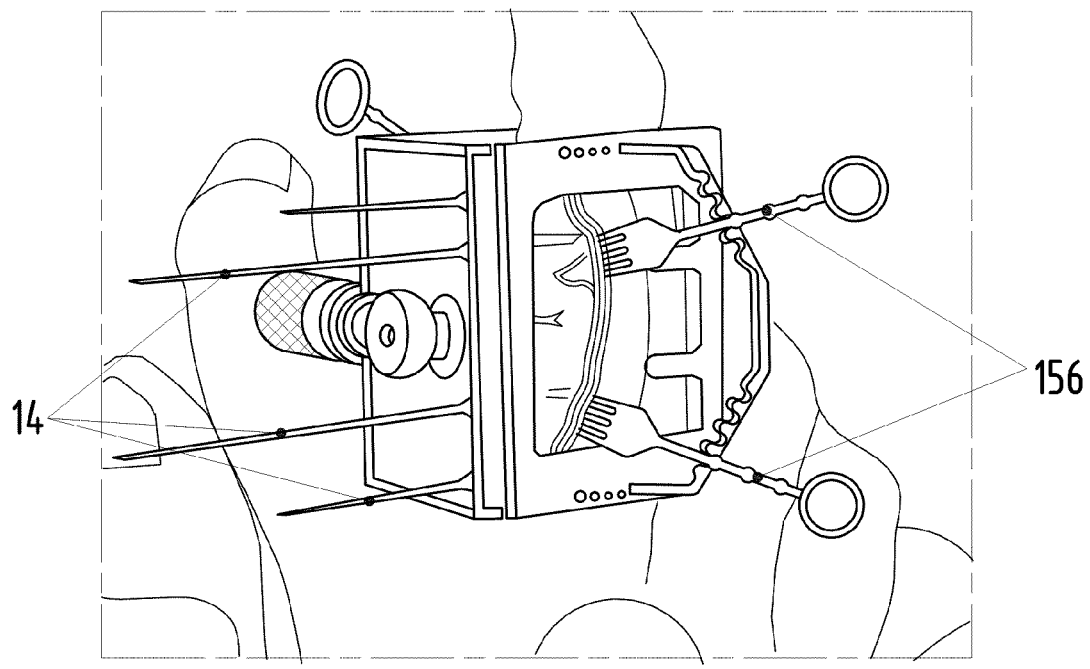

FIG. 9 shows the positioning operation by way of the rotary axis target device for precisely milling out the joint cylinder in accordance with the established rotary axis and FIG. 10 shows fixing of the fixing frame 12 according to the invention as a means for fixing the finger 2 in the straight position by way of four Kirschner wires 14 in predetermined holes in the drilling slide 16 on the base and middle phalanges. The fixing frame 12 can additionally be provided with a holding hoop 162 bridging thereover on the top side, for receiving and fixing retractor wound hooks 156. In that respect the wires 14 must engage the countercorticalis. The correct position of the fixing frame 12 is ensured by way of a centering sleeve 18 which can be fitted into a drilling slide 16, by way of a rotary axis aiming wire 8.

Figure 11:
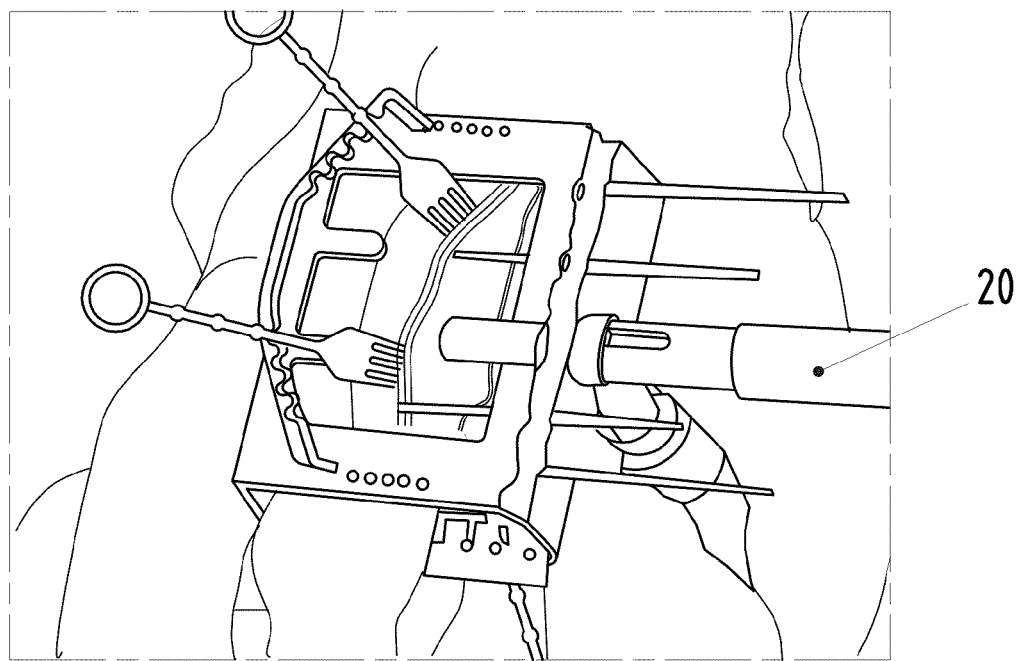
Figure 12:
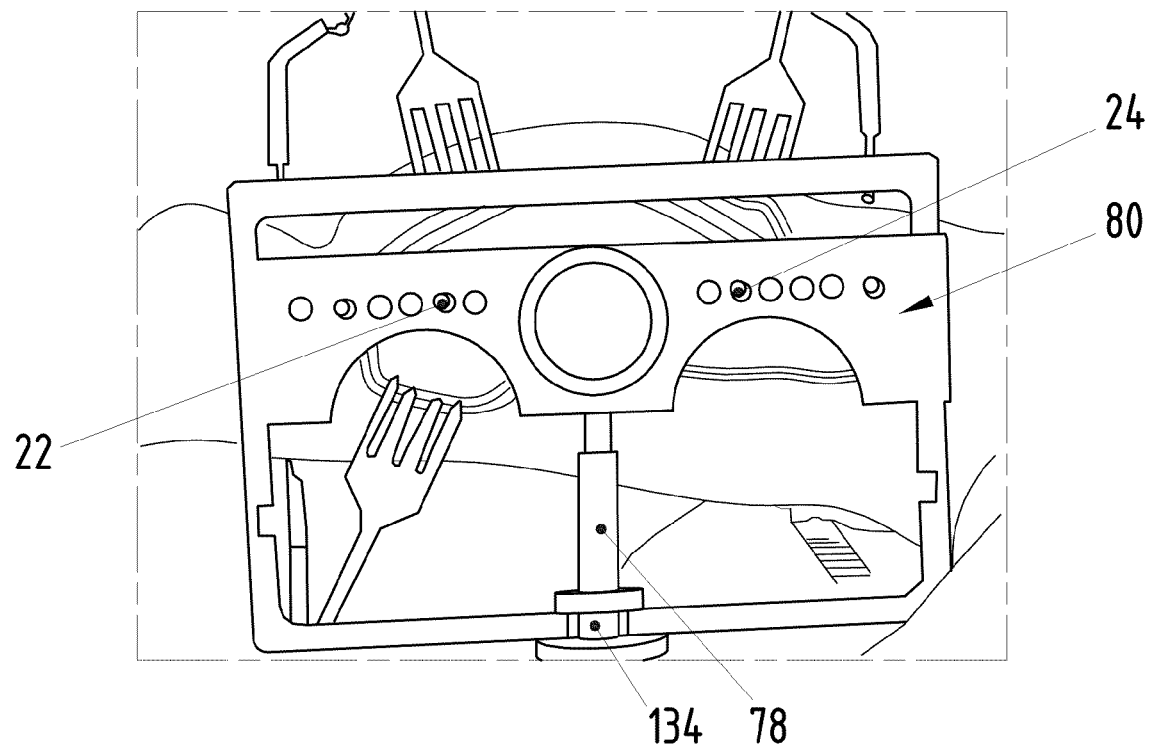

Now, referring to FIGS. 11 and 12, the joint 4 can be milled out with a cylindrical joint milling cutter 20 after removal of the centering sleeve 18 and the rotary axis aiming wire 8. In that case the operator can very well feel the milling depth with the finger on the contralateral side of the joint 4, and check the situation there. The milled-out joint cylinder is already removed in FIG. 12.

Figure 13:
Figure 14:
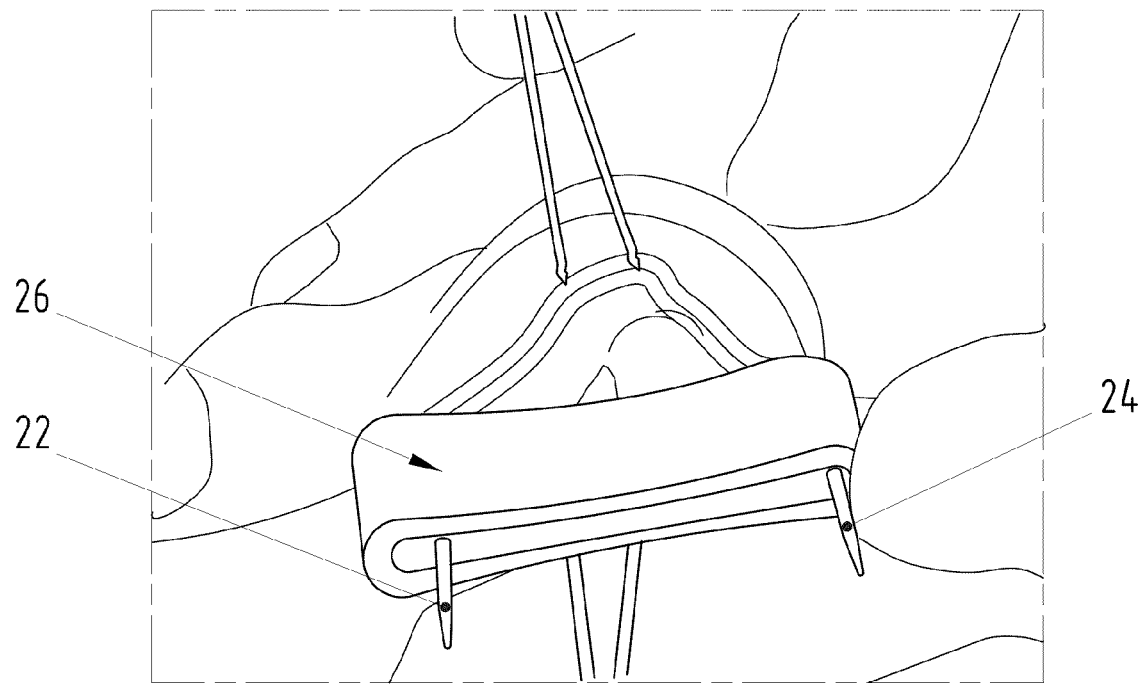
Figure 15:
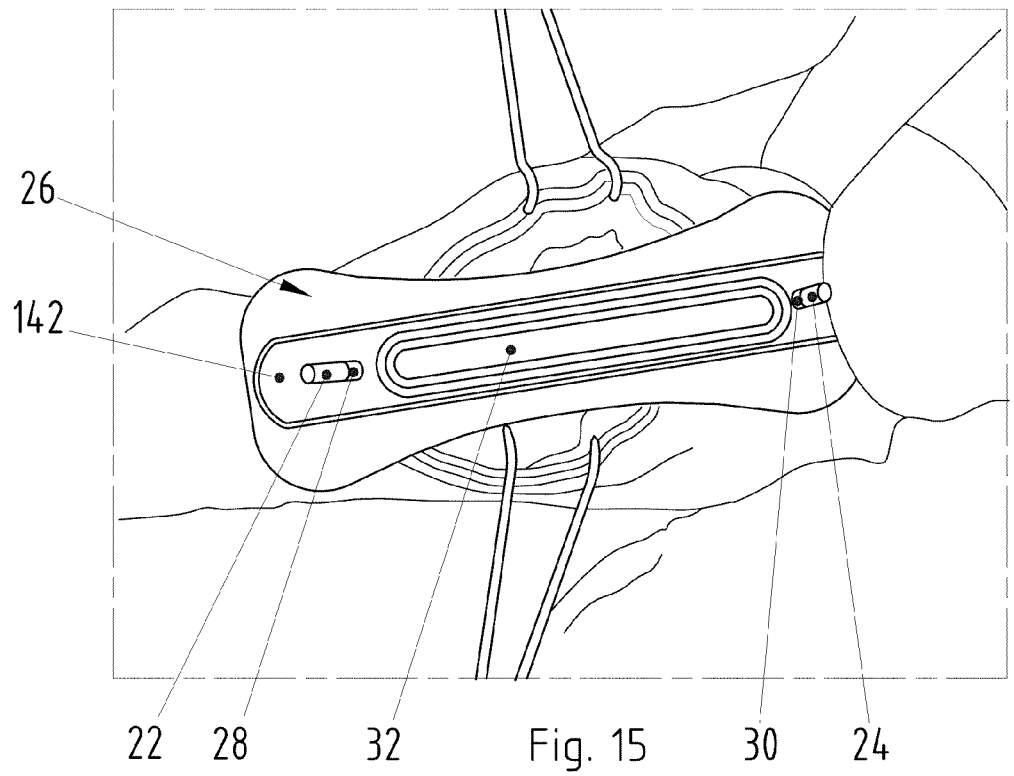

In FIG. 13 the respective outer fixing wires 22, 24 have remained, the fixing frame 12 has been removed to provide space for the milling gauge (FIGS. 14 and 15). That milling gauge is in the form of an elongate metal block which on the outside has slots 28, 30 for the fixing wires 22, 24. A guide slot 32 extending in the longitudinal direction is provided between those slots 28, 30. That guide slot 32 is adapted to receive a sawing block 144 which also has a sawing slot 154 extending in the longitudinal direction in relation to the block 144, for guiding a stepped saw 34. The milling gauge 26 serves as a 'template' for correct slot milling in the middle and base phalanges of the finger 2 for receiving the respective prosthesis arm.

Figure 16:
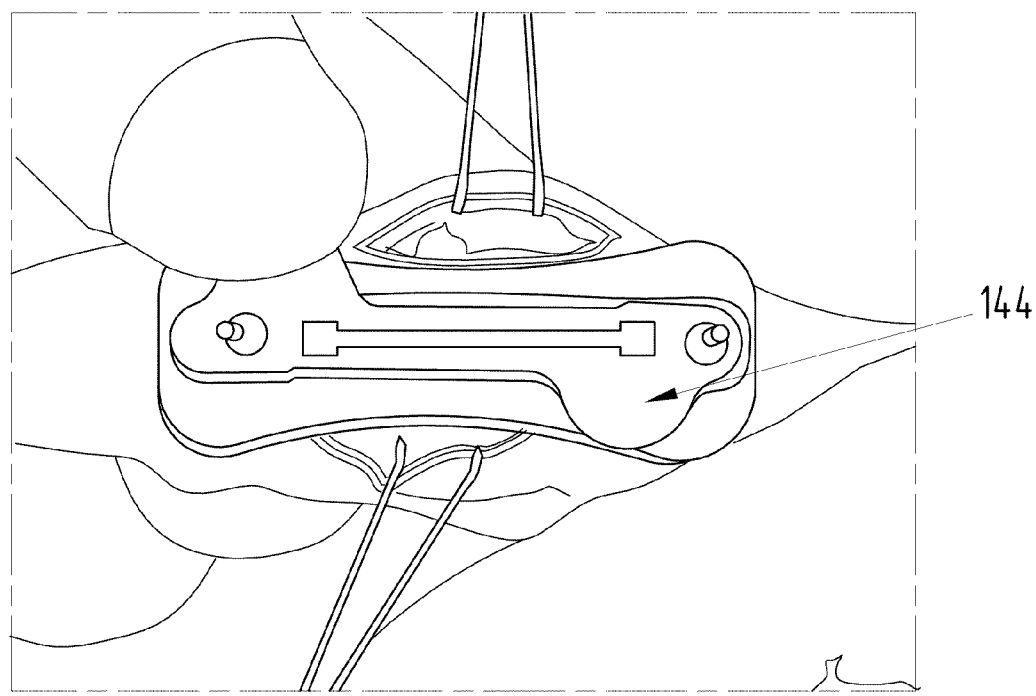
Figure 17:
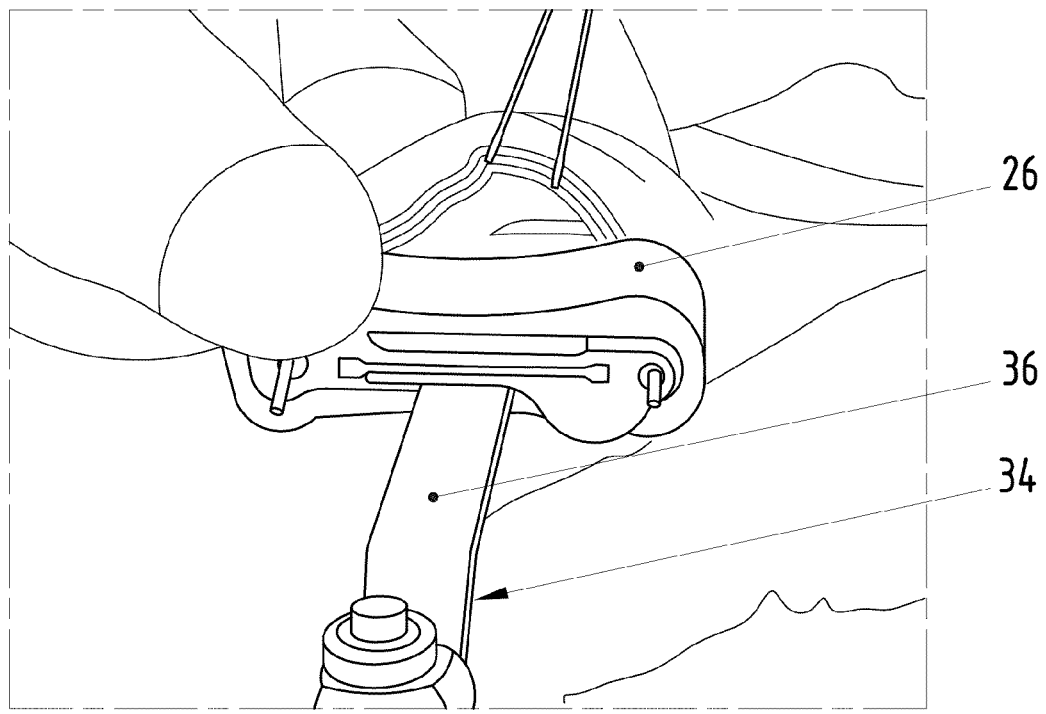
Figure 18:
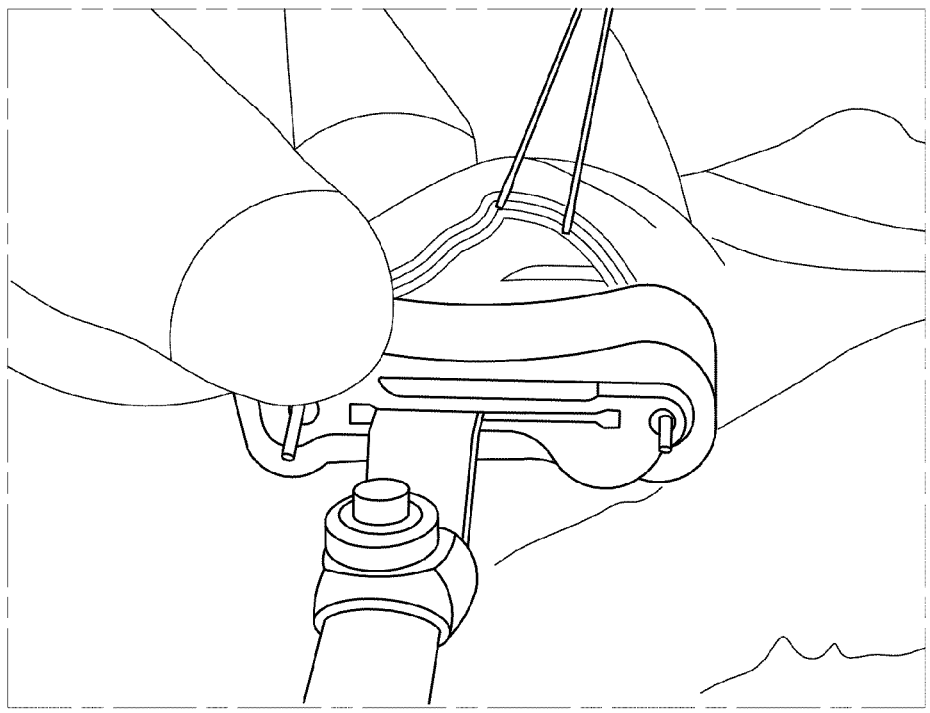
Figure 21:
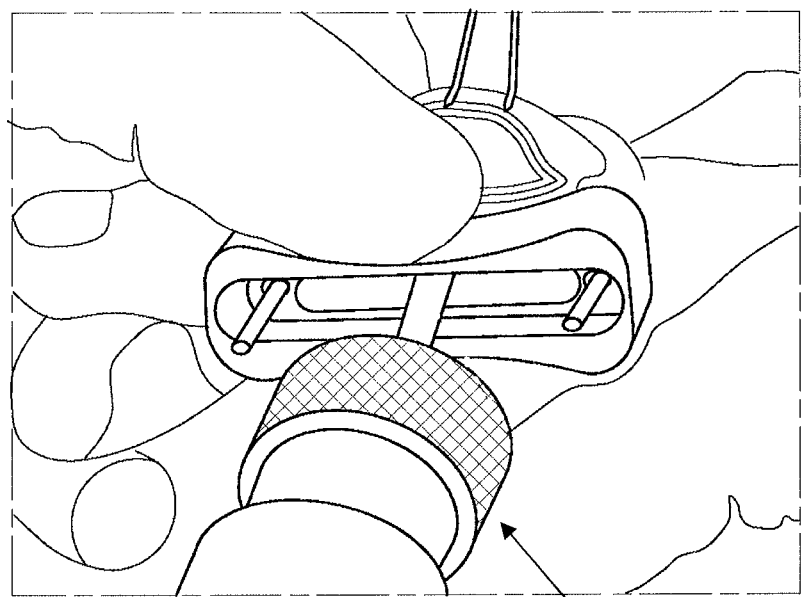
Figure 22:
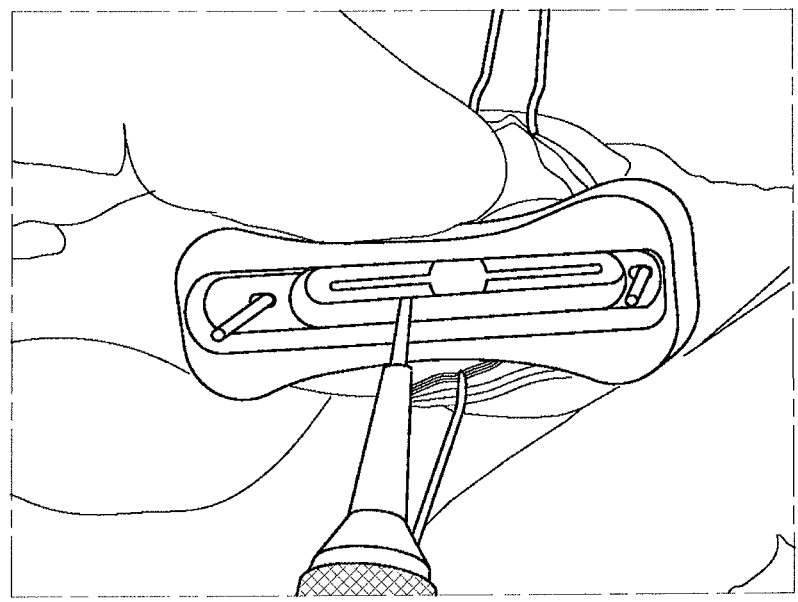

In FIG. 16, the milling gauge 26 has been inserted, by way of which the hard corticalis of the middle and base phalanges is 'broken' by way of the stepped saw 34 shown in FIG. 17. That saw 34 comprises an angled saw blade 36, with a saw surface 38 at the front end. The slot milling operation is markedly facilitated therewith (FIGS. 17 and 18).

In FIG. 19, it is possible to clearly see, after removal of the sawing block, the sawn slot 40, by way of which, with a now predetermined direction, the slot can be increased stepwise to the necessary depth and width with the milling cutter 20, as shown in FIG. 20.

The guide for the milling cutter 20 is of such a configuration that tilting is prevented. The milled slot 44 which is enlarged through the milling gauge can be clearly seen in FIG. 24.

In FIG. 23 the bony mounting for the endoprosthesis is now prepared. It can be clearly seen from FIG. 24 that the flexing and extension apparatus can be left completely intact!

Figure 25:
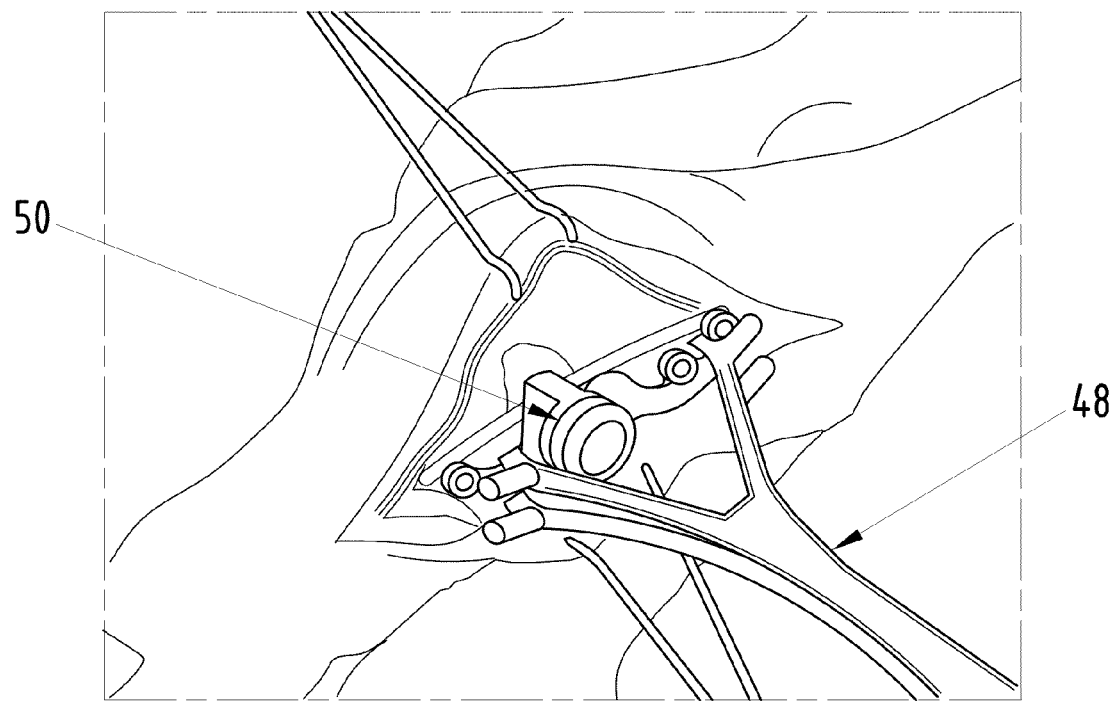

Referring to FIG. 25, the hinge prosthesis 50 is now inserted in the straight position, with the prosthesis holding forceps 58 according to the invention.

If a post-improvement to the bony prosthesis mounting 50 should still be necessary, either for post-milling of the slots or for the resection of bones at the respective palmar bone edge in relation to the prosthesis cylinder (free space is important for enabling flexing capability!) the endoprosthesis 50 can be removed again with the extraction instrument 52 according to the invention without in that case damaging the prosthesis 50.

Figure 27:
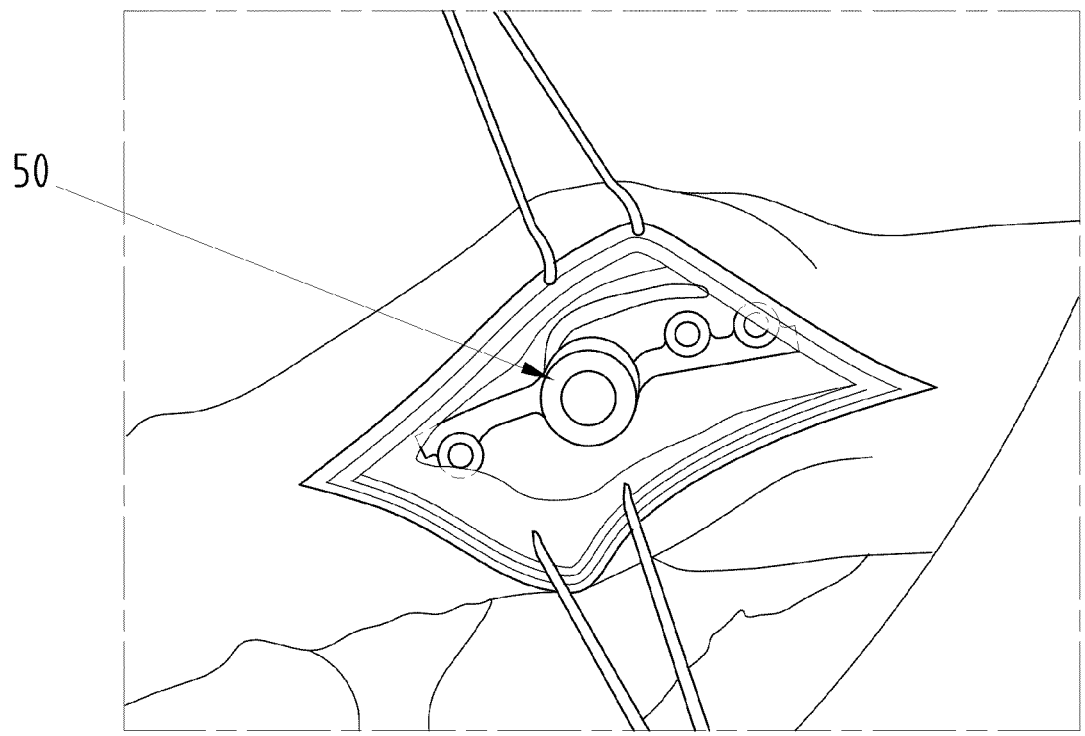
Figure 28:
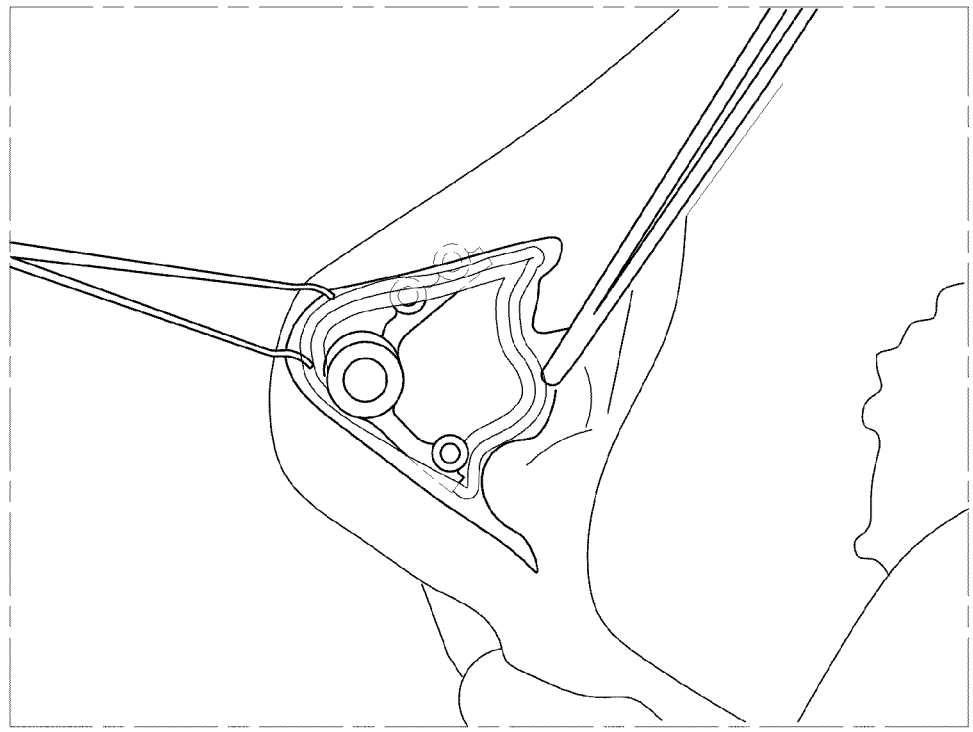
Figure 29:
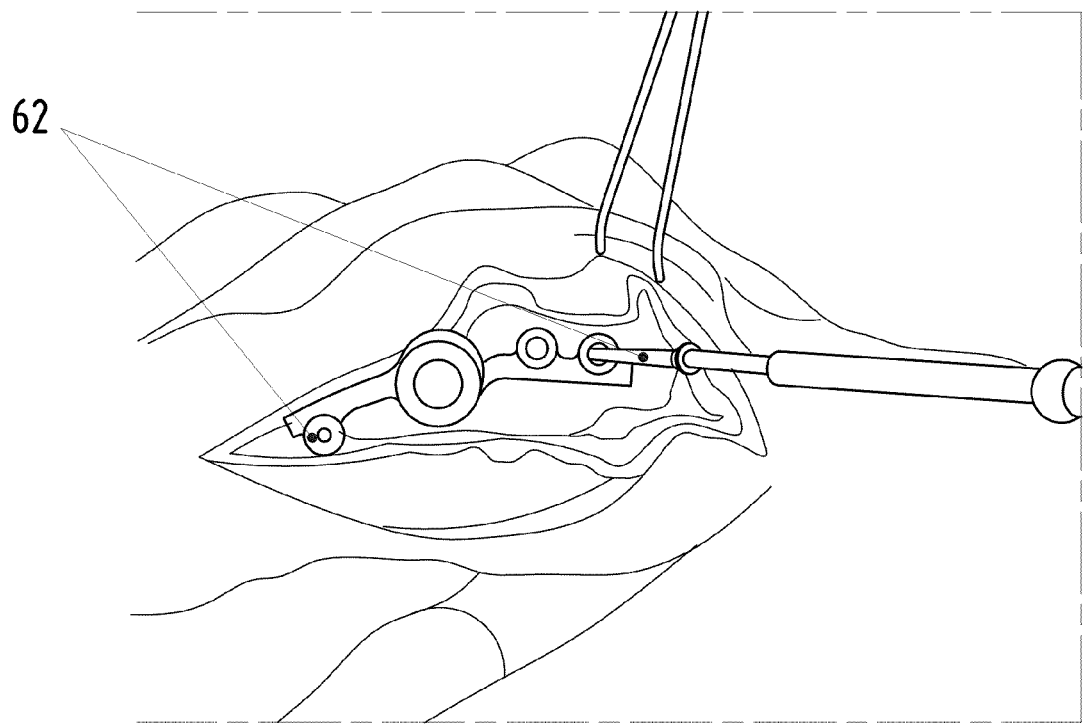
Figure 30:
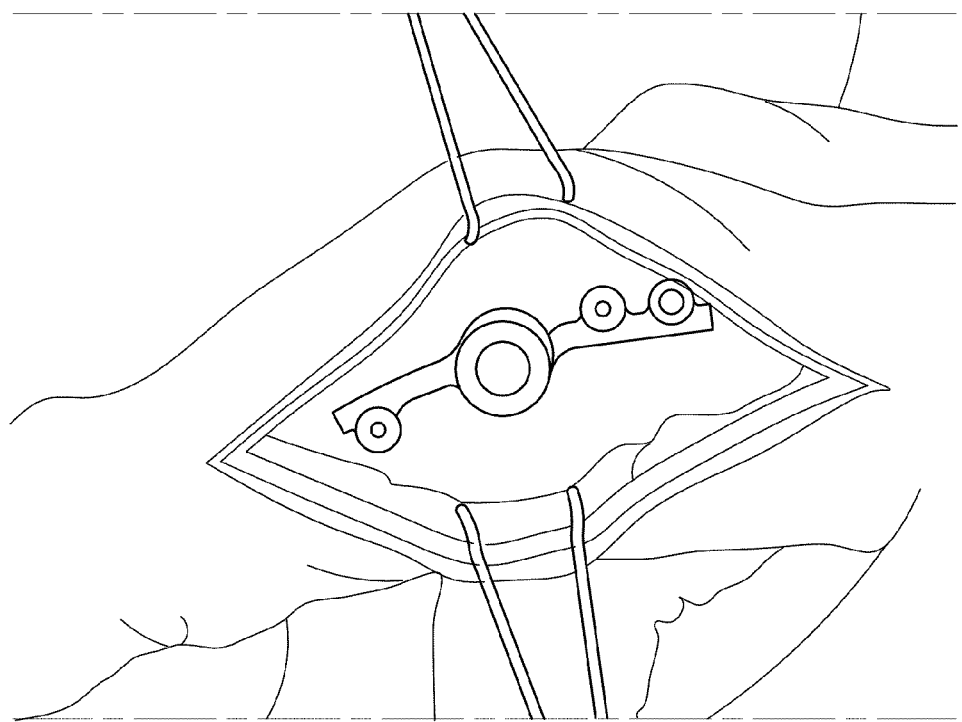
Figure 31:
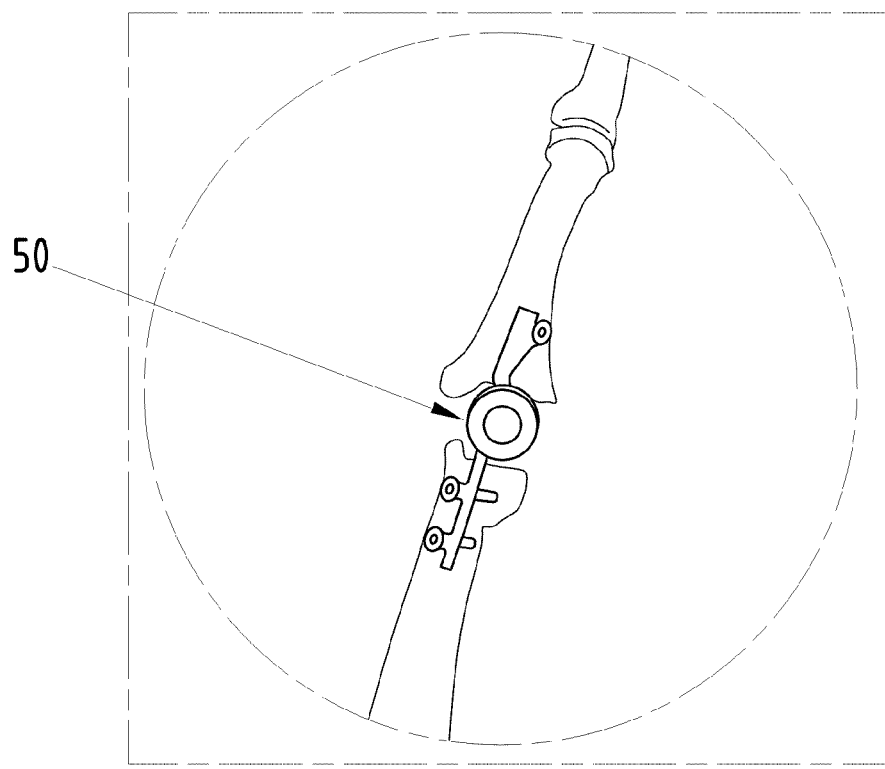
Figure 32:
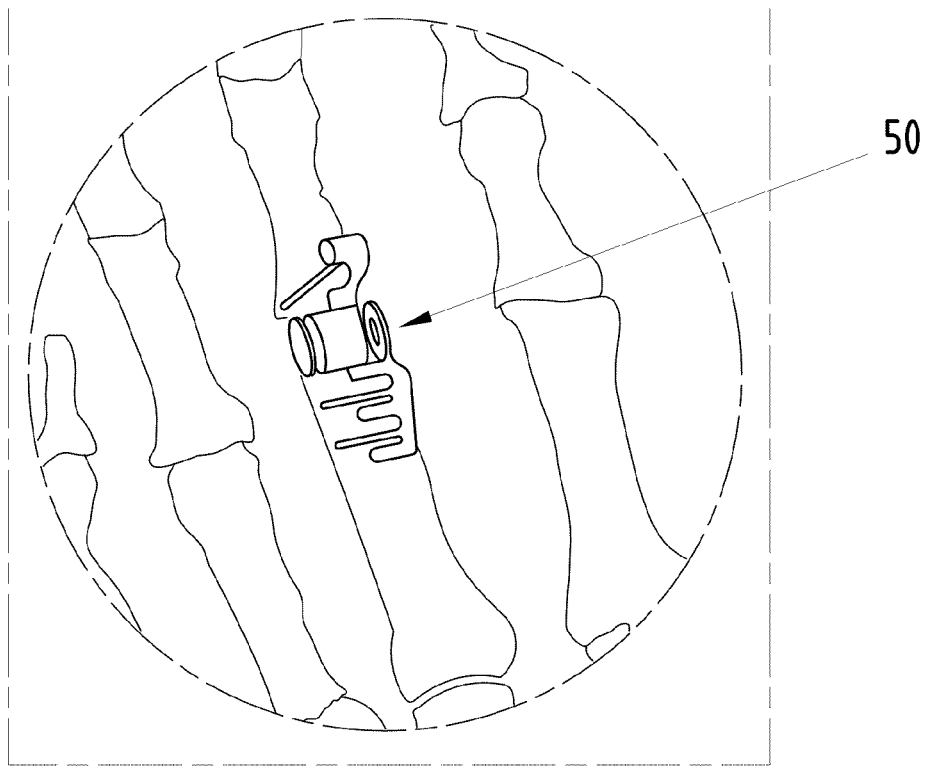

The endoprosthesis 50 is correctly inserted in the straight position at the left in FIG. 27, and the flexing position is being checked in FIG. 28. That position properly attains 90 degrees and it is only then that the movement is impeded by bone contact.

Although the endoprosthesis 50 is inserted with a press fit, it is anchored distally in the short arm and proximally in the long arm with a respective titanium screw 62 fixedly in the bone. That permits early, non-loaded functional exercise of the joint.

Figure 33:
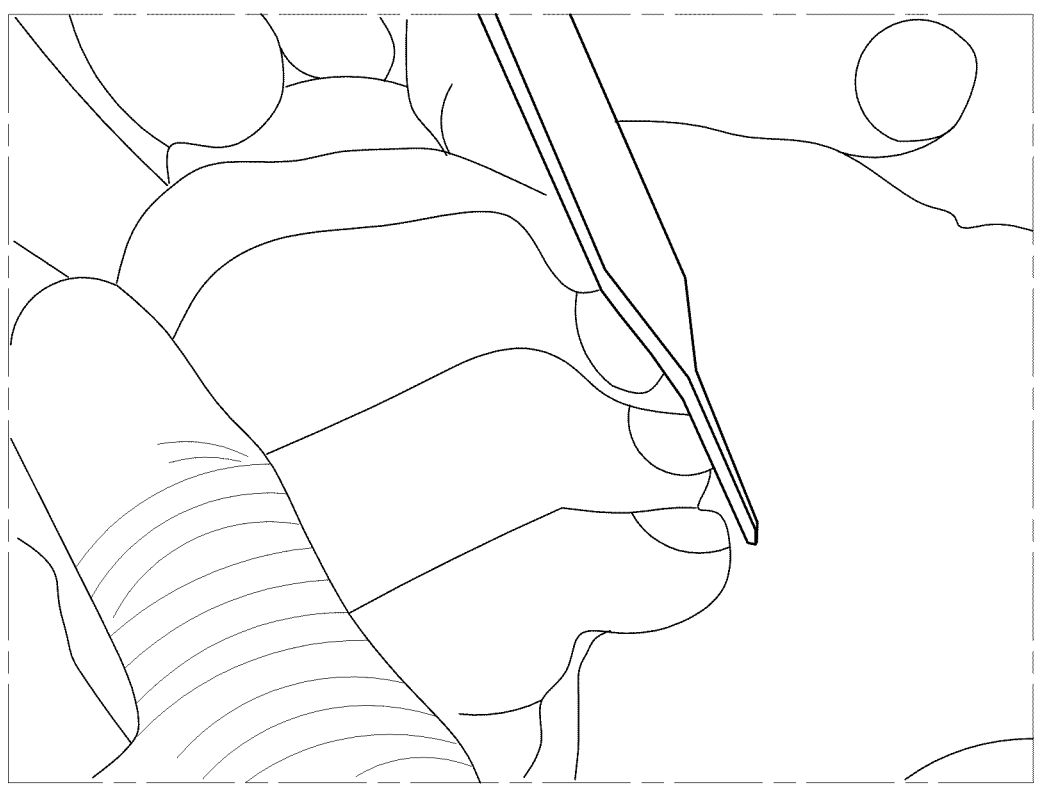
Figure 34:
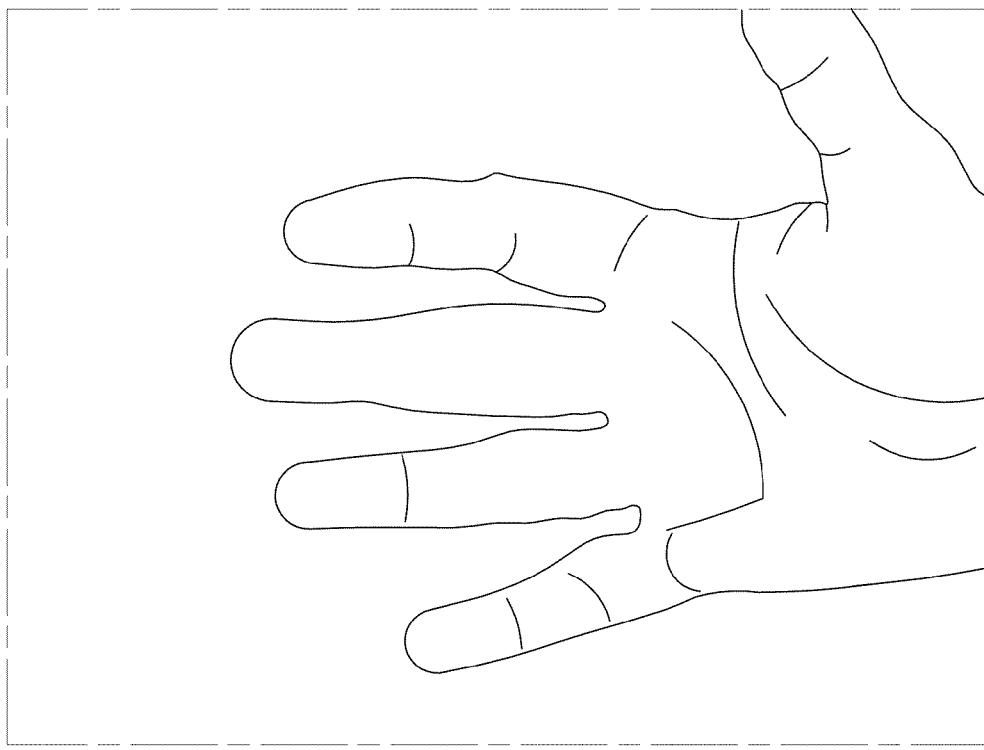

As shown in FIGS. 33 and 34 the position of the endoprosthesis 50 is checked in both planes and documented by means of the X-ray image converter, before closure of the wound.

Figure 35:
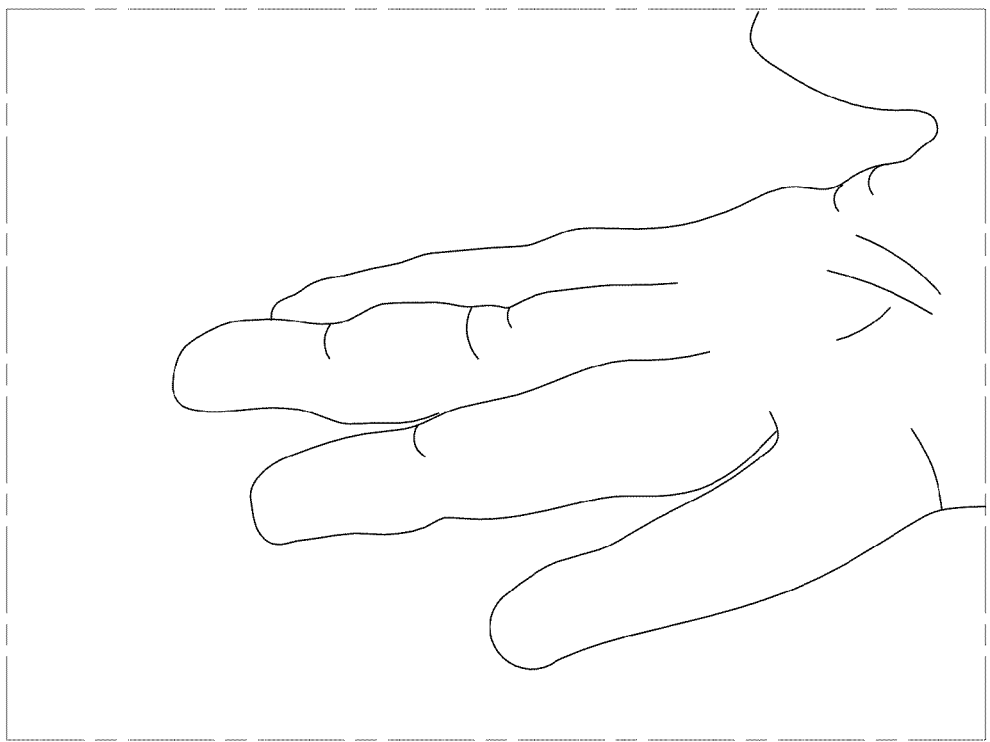

Referring to the view in FIG. 35, after closure of the wound the clinical flexing function is checked: free flexing without rotational errors.

Figure 36:
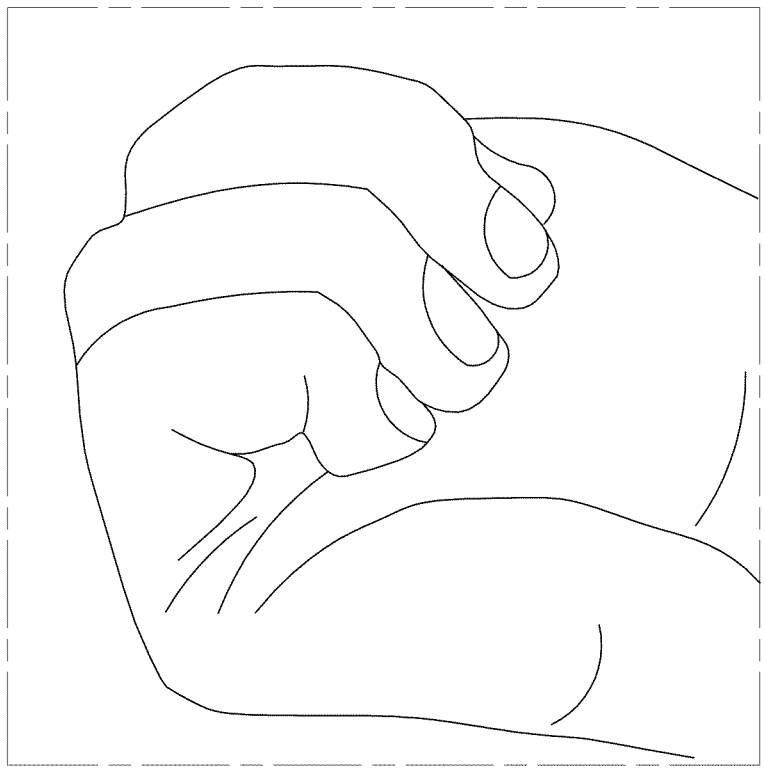
Figure 37:
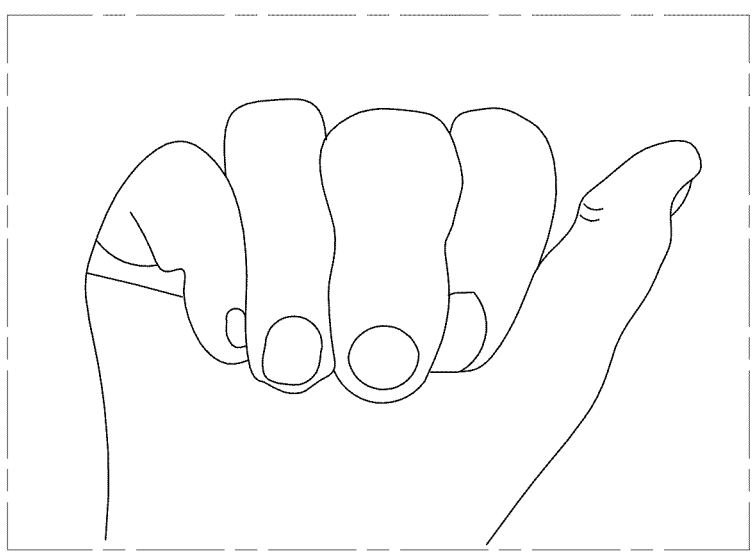

FIG. 36 shows the hand operated on, 8 weeks after the operation; the middle finger 2 is only still slightly swollen and active extension is free as shown in FIG. 37. Finally the flexing shown in FIGS. 36 and 37 is better than in the preoperative condition. That very good function is in particular pain-free!

Figure 38:
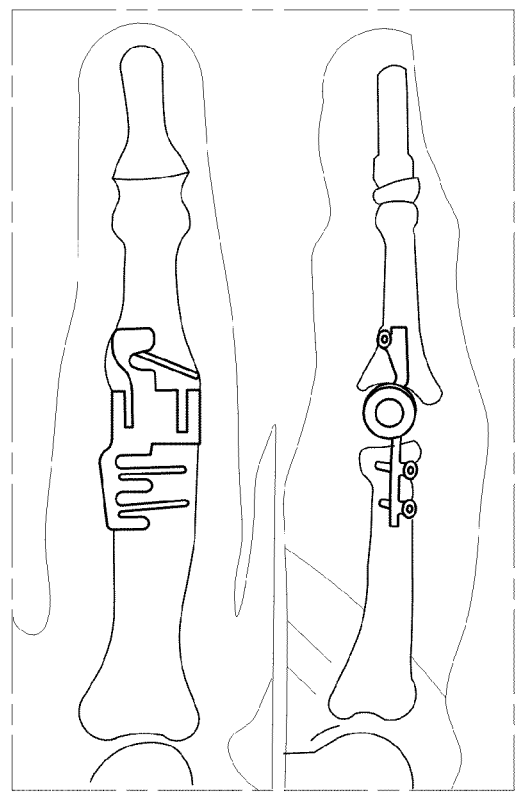
Figure 39:
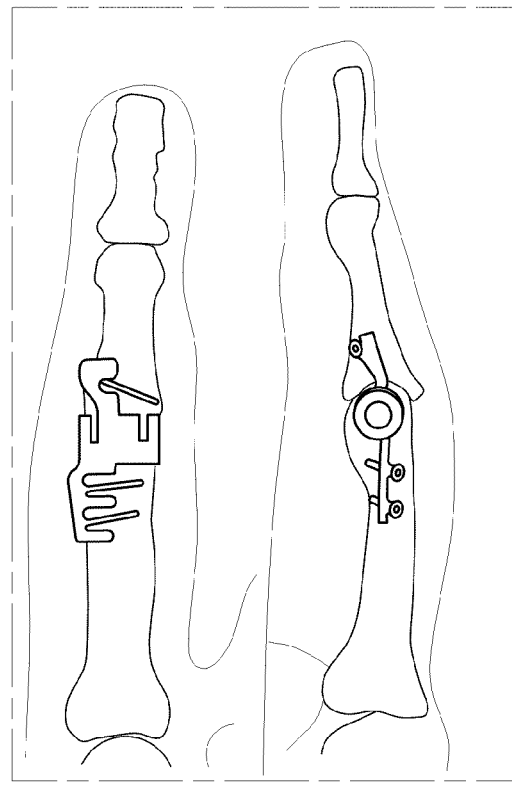

By an X-ray examination FIGS. 38 and 39 show post-operatively no lysis symptoms post-operatively four weeks (FIG. 38) and eight weeks (FIG. 39), and the calcium salt content increases.

Figure 40:
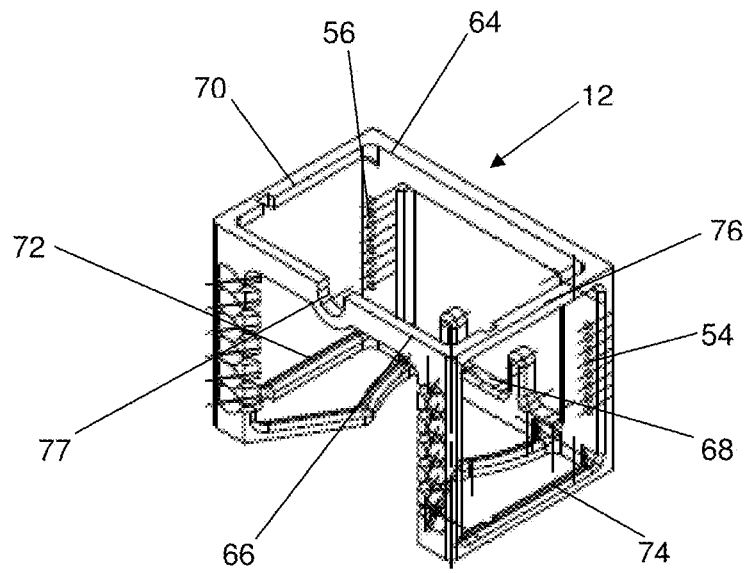
FIG. 40 shows a perspective view of a fixing frame.
Figure 41:
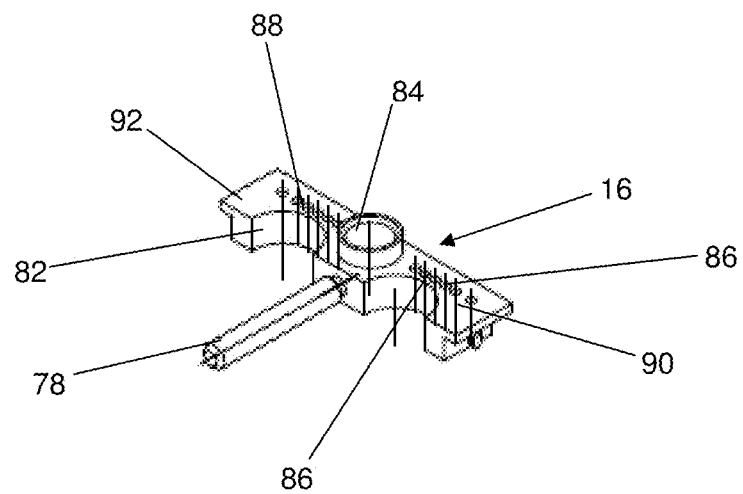
FIG. 41 shows a perspective view of a drilling slide.
Figure 42:
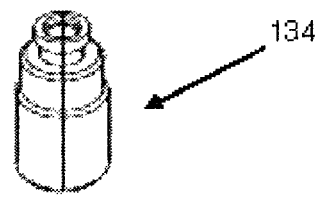
FIG. 42 shows a perspective view of an adjustment nut of the size M4.
Figure 43:
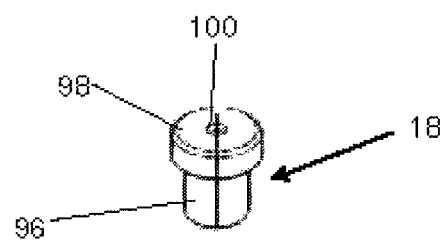
FIG. 43 shows a perspective view of a centering sleeve.

The instruments used and shown in detail in FIGS. 40 to 42 are made from medical high-quality steel.

FIGS. 40 to 52 show the individual component parts of the instrument set according to the invention for carrying out the operating procedure according to the invention.

FIG. 40 shows a perspective view of the fixing frame 12 which is made from surgical high-quality steel and has a rigid main frame defining a box-like receiving space, with a plurality of longitudinal bars 64, 66, 68 extending parallel to each other in the longitudinal direction and transverse bars 70, 72, 74, 76 extending transversely with respect to the longitudinal bars and also extending parallel to each other. Formed between the bars 64-76 extending only at the edges are openings so that the interior of the fixing frame 12 is accessible to the operator at all sides. The fixing frame 12 can also be formed with a bridge-shaped hoop 162 which is shown on an enlarged scale in FIG. 51 and which extends over the dorsal opening, having a plurality of mutually juxtaposed receiving recesses 164 for receiving the wound hooks 156 shown in FIG. 50. For that purpose, insertion openings 54, 56 are provided at the dorsal side of the fixing frame 12 on both sides of the upper opening.

Figure 44:
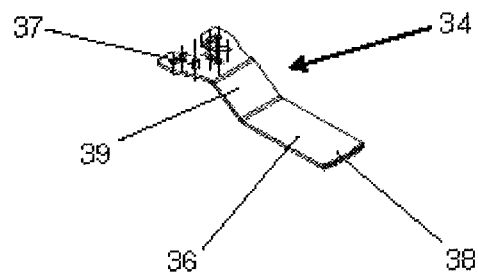
FIG. 44 shows a perspective view of a saw blade.

In the middle the longitudinal bar 66 has a semicircular recess 77 into which an adjusting nut 134 shown on an enlarged scale in FIG. 44 can be rotatably inserted. Screwed into the central screwthread opening 136 of that adjusting nut 134 is a spacer bar 78 of the drilling slide 16, by means of a corresponding male screwthread, so that rotary movement of the adjusting nut 134 produces a defined adjusting movement of the drilling slide 16 in relation to the fixing frame 12.

The drilling slide 16 has a positioning bar 82 which extends in the longitudinal direction and which centrally has a guide opening 84 extending transversely therethrough for receiving the guide sleeve 18 or the joint milling cutter 20 and, laterally of that guide opening 84, positioning holes 86, 88 for the fixing wires 22, 24. The ends of the positioning bar 82 are each formed with a respective right-angled guide abutment 90, 92 which in the installation position bear at the inside and the top side against the transverse bars 70, 76 for affording parallel guidance for the drilling slide 16 on the fixing frame 12 in the adjustment movement. The positioning openings 86, 88 serve for inserting the fixing wires 22, 24 into the finger bones in accurate positions.

Figure 45:
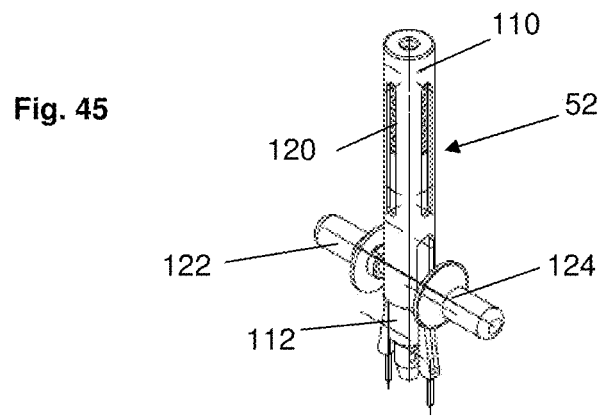
FIG. 45 shows a perspective view of an extraction tool.
Figure 46:
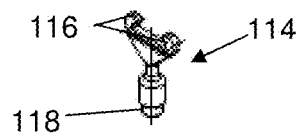
FIG. 46 shows a perspective view of a clamp for connection to the proximal end of the extraction tool.

The centering sleeve 18 which is shown on an enlarged scale in FIG. 45 can be inserted into the guide opening 84 of the drilling slide 16. That centering sleeve comprises a cylindrical metal body, the outside diameter of which corresponds to the inside diameter of the guide opening 84 and which, at its upper end in FIG. 47, has a radially outwardly enlarging shoulder 98 which in the installation position bears at the outside against the guide opening 84 of the drilling slide 16. Centrally the centering sleeve 18 has a receiving opening 100 extending therethrough for the rotary axis aiming wire 8.

The saw blade 102 which is shown on an enlarged scale in FIG. 44 and which is of a double-angled configuration, for breaking open the corticales comprises a double-bend metal plate 103 which extends in the longitudinal direction and which is of a thickness of preferably 0.64 mm, having a saw 104 at its front cutting end. At the rear fixing end the saw blade has a semicircular fixing ring 37 for being clamped in a gripping device. From the plane of the saw blade 36 which extends from the front sawing surface 38 to the fixing ring 37 it is angled upwardly approximately at three quarters of the distance involved, preferably through about 36 degrees, to form a step 39, and then goes to the fixing ring again into an end extending parallel to the front portion, so that a double-bent saw blade 36 with a central step 39 is formed. That step 39 forms an abutment when the saw blade 36 is pushed into the slot of the saw block 144 shown in FIG. 51 (see also FIG. 18).

Figure 26:
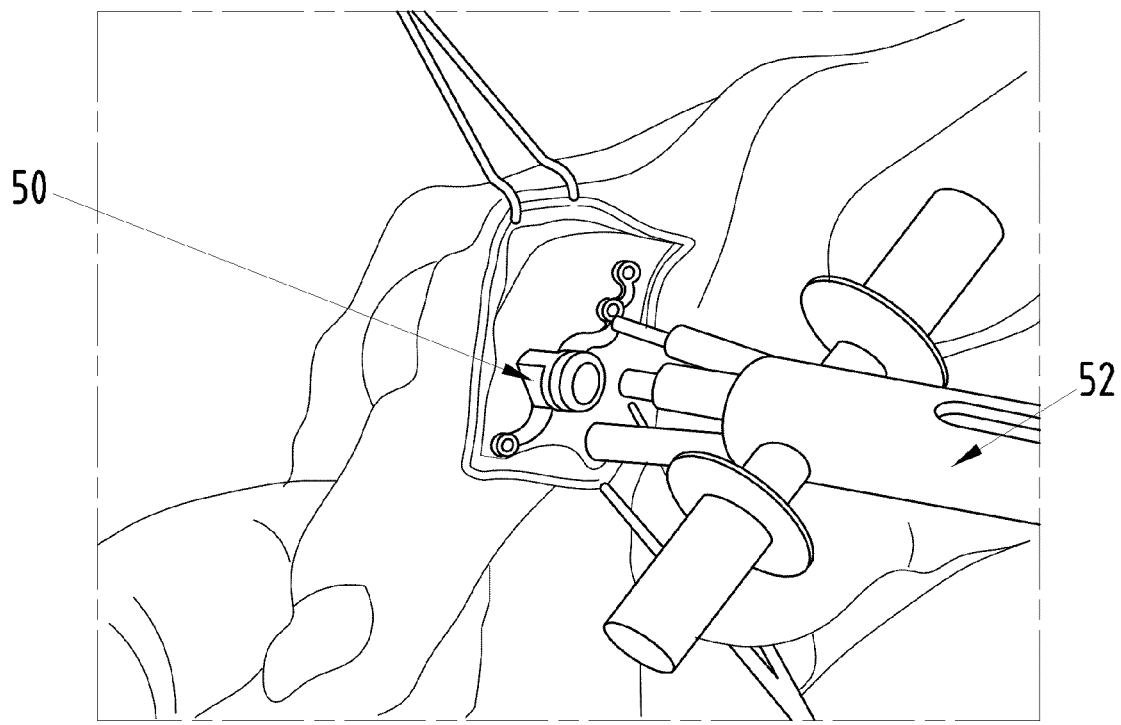

FIG. 45 shows a perspective view on an enlarged scale of the extraction instrument 52 for removing the finger joint prosthesis after placement in a finger. The extraction instrument 52 comprises an outer hollow body 110 which is adapted for relatively movably receiving a slider 112 arranged therein. The clip 114 shown on an enlarged scale in FIG. 44 can be screwed to the proximal end of the slider 112. The clip 114 has hooks 116 which project radially towards each other in diametrically opposite relationship and which are hookable in the outer peripheral frame of the joint prosthesis 50. The lower end of the clip 114 has a male screwthread 118 which can be screwed into the lower proximal end of the slider 112. In that way the extraction instrument 52 according to the invention, by changing the clips 114, can be easily converted for extracting finger joint prostheses of different sizes, involving different outside diameters. A coil spring 120 is operative between the upper end of the slider 112 and the inside of the hollow body 110. Actuation of the extraction instrument 52 is effected by way of two laterally radially protruding gripping members 122, 124 which are screwed in place. By relative movement of the gripping members 122, 124 in relation to the hollow body 110 (see FIG. 26) against the spring force of the coil spring 120, the slider 112 is moved in relation to the hollow body 110 to remove the joint prosthesis from the finger gently.

Figure 47:
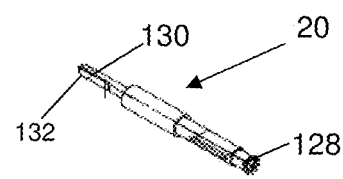
FIG. 47 shows a perspective view of a joint milling cutter.

FIG. 47 shows the joint milling cutter 20 according to the invention, comprising a cylindrical metal body of hardened high-quality steel. At the front end the joint milling cutter 20 is equipped with a milling head 128 and thereafter extending towards the fixing end goes into two radial enlargement portions, wherein the adjoining insertion end 130 for insertion into the drilling machine narrows markedly once again in relation to the central region of greatest width. The insertion end 130 is formed in the region of the rear portion with a peripherally extending groove 132 for fixing in the drilling machine in positively locking relationship.

Figure 48:
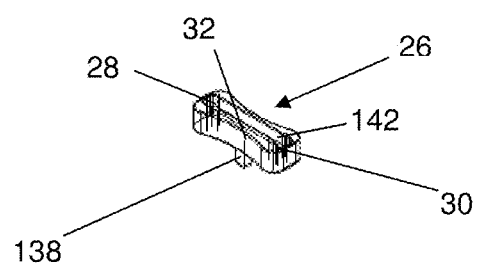
FIG. 48 shows a perspective view of a milling gauge.
Figure 49:
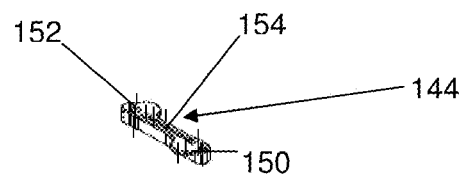
FIG. 49 shows a perspective view of a slotted sawing block.

FIG. 48 shows a perspective view of the milling gauge 26 according to the invention which substantially comprises a high-quality steel block which is bone-shaped in a front view, of a length of about 45 mm, a height of about 20 mm and a width of about 19 mm. A centering pin 138 for insertion into the joint bore is provided at the rear centrally on the longitudinal side. In the direction of its longitudinal extent, the milling gauge 26 has the guide slot 32 for guiding the milling cutter 20. Also on the front side, the milling gauge 26 has a slightly larger trough-shaped recess 142, into which the saw block 144 shown as a perspective view in FIG. 51 can be inserted. Also provided on the milling gauge 26 on both sides beside the guide slot 32 are slots 28, 30. Those slots serve as tolerance compensation to prevent unwanted tilting upon non-aligned placement on the Kirschner wires 14 fixed on both sides of the joint bore in the finger. The saw block 114 is accordingly also provided with positioning openings 150, 152 which extend transversely with respect to the longitudinal direction and which in the installation position in the inserted condition in the front recess 142 of the milling gauge 136 sit on the Kirschner wires 14. Extending in the longitudinal direction between the positioning openings 150, 152, the saw block is provided with a saw slot 154 serving as a guide for the saw blade 36 shown in FIG. 46. In that respect the cranked central portion 104 of the saw blade bears on the outside against the front side of the saw block 144 and thereby limits the depth of penetration of the saw blade 36.

Figure 50:
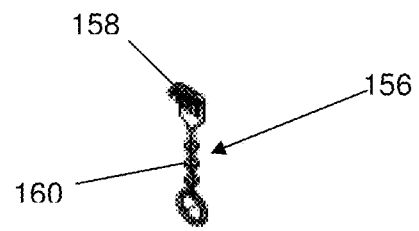
FIG. 50 shows a perspective view of a retractor wound hook.
Figure 51:
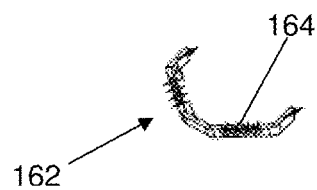
FIG. 51 shows a perspective view of a holding clip for connection to the fixing frame.

FIG. 50 shows a perspective view on an enlarged scale of the substantially bar-shaped wound retractor hook 156 which at its front end has a plurality of claw-like fingers 158 extending in parallel relationship, for hooking engagement into the tissue. The longitudinal shank of the wound hook 156 has at regular spacings ball-shaped enlarged portions 160 which are hookable in various positions as shown in FIGS. 9 to 12 into the holding loop 162 which is shown as a perspective view in FIG. 53.

That holding loop 162 comprises a high-quality steel arcuate portion which is bent substantially in a U-shape and which at its free ends has pin-shaped projections for insertion into the insertion openings 54, 56, at the top side, of the fixing frame 12. In the installation position the holding loop 162 extends bridge-like over the upper opening of the fixing frame 12 in the manner shown in FIGS. 9 to 12. The holding loop 162 is provided at its front side with a plurality of regularly spaced receiving recesses 164, each of those receiving recesses 164 being only slightly wider than the width of the shank of the wound hook 156.

FIG. 52 shows a perspective view on an enlarged scale of the rotary axis aiming device 10 used in FIGS. 6 to 8. Substantially it comprises a cylindrical central element for receiving an aiming wire 8, from the outer peripheral surface of which extend a proximal directional bar 170 and a distal directional bar 172, with the inclusion of an angle of about 120 degrees. The directional bars 170, 172 each include respective radial extension portions which extend radially outwardly from the central element and which define a first vertical plane, and then go at an angle of 90 degrees into axial extension portions which extend at a spacing relative to the centre line of the central element and define a horizontal plane.

In the present embodiment the central element comprises an inner ring 168 extending in co-linear relationship with the longitudinal direction, for receiving the aiming wire 8, with three connecting struts extending spoke-like therefrom to an outer ring 169. The inside diameter of that outer ring 169 corresponds to the outside diameter of the hinge prosthesis 50. Formed integrally on the outer ring are the proximal directional bar 170 and the distal directional bar 172, with the inclusion of an angle of about 120 degrees therebetween. They firstly extend with radial extension portions radially outwardly and then go at an angle of 90 degrees into axial extension portions extending coaxially with the centre line of the inner ring 168.

With the rotary axis aiming device 10 the operator, using the image converter, can determine the correct orientation of the aiming wire 8 and the directional bars 170, 172 in the axial direction. The operator can determine the position of the rotary axis aiming device, at the inside of the outer ring. When the orientation is correct, the operator sees the joint gap of the bone and the correct dorsal and radial orientation of the directional bars 170, 172.

As mentioned hereinbefore all component parts of the instruments according to the invention are preferably made from a surgical high-quality steel. The set of instruments is usually presented to the operator in an apertured insert holder, the corresponding openings in the drilling slides, the centering sleeves, the rotary axis aiming devices and the joint milling cutters preferably being of diameters of 6, 7 and 8 mm.

Although the invention has been described by reference to a finger joint the advantages according to the invention can also be achieved in regard to the placement of implants in other joints.

The subject-matter of the present invention arises not only out of the subject-matter of the individual claims but also the combination of the individual claims with each other. All features and details disclosed in the documents—including the Abstract—, in particular the three-dimensional configurations shown in the drawings, are claimed as essential to the invention insofar as they are novel individually or in combination over the state of the art.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An instrument set for performing a procedure on a finger joint of a finger, the instrument set comprising:
a fixing frame having longitudinal bars and transverse bars defining a box-like space into which the finger is insertable and within which the finger is fixable to a restraint;
a drilling slide having a positioning bar extending in a longitudinal direction and a spacer element extending in a transverse direction, the positioning bar including a guide opening extending transversely therethrough and a plurality of positioning holes;
a centering sleeve having a cylindrical main body adapted for insertion into the guide opening, the main body having a peripherally extending shoulder and a receiving opening for an aiming wire; and
a rotary axis aiming device including an inner ring sized and configured to receive the aiming wire and two directional bars.

2. Instruments according to claim 1 wherein the spacer element extends transversely with respect to the positioning bar, the spacer element configured to selectively fix the positioning bar in any one of a plurality of predetermined reference positions in relation to the fixing frame.

3. Instruments according to claim 1 further including a stepped saw having a fixing end releasably fixable to a grip and a saw surface at a cutting end in opposite relationship to the fixing end, the stepped saw further including a step between the fixing end and the cutting end.

4. Instruments according to claim 3 wherein the step extends at an angle of about thirty-six degrees)(36° relative to a plane defined by one of the fixing end and the cutting end.

5. Instruments according to claim 1 further including an extraction instrument having a hollow body extending in a longitudinal direction; and a spring-loaded slider receivable in the hollow body and movable by way of at least one actuating element in relation to the hollow body, a proximal end of the slider having a mount to which a clip is fixable.

6. Instruments according to claim 5 wherein the actuating element includes two gripping members which project radially laterally in mutually opposite relationship and which are connected to the spring-loaded slider.

7. Instruments according to claim 6 wherein the gripping members are screwably attachable the spring-loaded slider.

8. Instruments according to claim 1 further including a joint milling cutter having a cylindrical milling cutter body which at an insertion end is receivable in a drilling machine and which at a milling end opposite to the insertion end has a milling head.

9. Instruments according to claim 1 further including a milling gauge including an elongate block body; fixing wire slots in the elongated body; a guide slot positioned between the fixing wire slots extending in the longitudinal direction for receipt of a milling cutter and a receptacle for a saw block which includes a saw slot.

10. Instruments for carrying out an operating procedure on a finger joint of a finger of a patient, the finger joint having a rotary axis, the instruments comprising:
(i) a fixing frame comprising:
a plurality of bars, each bar permanently immovable relative to each other bar,
a receiving space formed by the plurality of bars and into which the finger is insertable and within which the finger is fixable by a restraint, and
a lateral side with an access through which the finger joint is accessible during the operating procedure; and
(ii) a drilling slide comprising:
a positioning bar slideably coupled to the lateral side of the fixing frame,
a guide opening extending generally transversely through the positioning bar,
a plurality of positioning holes located in the positioning bar generally laterally from the guide opening and through which access into the receiving space is provided, and
a spacer element extending transversely from the positioning bar to one of the plurality of bars forming the fixing frame, the spacer element releasably fixing the positioning bar in any one of a plurality of selectable predetermined reference positions on the lateral side of the fixing frame.

11. The instruments of claim 10 further comprising: (iii) a centering sleeve insertable in the guide opening, the centering sleeve having a peripherally extending shoulder at one end and a centrally positioned bore.

12. The instruments of claim 11 further comprising: (iv) an aiming wire extendable through the bore of the centering sleeve when the centering sleeve is inserted in the guide opening.

13. The instruments of claim 10 further comprising: a rotary axis aiming device alignable with the rotary axis of the finger joint.

14. The instruments of claim 10 further comprising: a joint milling cutter relatively movably receivable in the guide opening.

15. The instruments of claim 10, wherein the restraint is a fixing wire engageable with the finger when the finger is in the receiving space and the fixing wire extends through one positioning hole of the plurality of positioning holes.

16. The instruments of claim 10 further comprising: a stepped saw having a fixing end releasably fixable to a grip and a cutting end in opposite relationship to the fixing end, the stepped saw further including a saw surface and a step formed between the fixing end and the cutting end.

17. The instruments of claim 10 further comprising: an extraction instrument having a hollow body extending in a longitudinal direction; a spring-biased slider receivable in the hollow body and is movable by way of at least one actuating element in relation to the hollow body, a proximal end of the slider having a mount to which a clip is fixable.

18. The instrument according to claim 14 wherein the joint milling cutter has a cylindrical milling cutter body with an insertion end receivable in a drilling machine and a milling end in opposite relationship to the insertion end has a milling head.

19. The instruments of claim 10 further comprising: a milling gauge including an elongate block body; fixing wire slots in the elongated body; a guide slot between the fixing wire slots extending in the longitudinal direction; and a receptacle for a saw block which includes a saw slot.

20. The instruments of claim 10 wherein the plurality of bars includes a plurality of longitudinal bars extending in a longitudinal direction and a plurality of transverse bars extending transversely relative to the longitudinal direction.

21. The instruments of claim 10 further comprising: at least one holding loop for fixing wound retractor hooks to the fixing frame.

22. Instruments according to claim 21 characterized in that the holding loop is releasably fixable to the fixing frame.

23. Instruments according to claim 20 wherein the longitudinal and transverse bars define a box-like space within which the finger is fixable in a straight position with the restraint.

24. The instruments of claim 10 wherein the fixing frame has a receiver and a guide for the drilling slide.

* * * * *